(12) United States Patent
Witney et al.

(10) Patent No.: US 7,271,886 B2
(45) Date of Patent: Sep. 18, 2007

(54) UNCAGING DEVICE

(75) Inventors: Frank Witney, Oakland, CA (US);
Gary McMaster, Ann Arbor, MI (US);
Quan Nguyen, San Ramon, CA (US);
Steve Chen, Fremont, CA (US)

(73) Assignee: Panomics, Inc., Fremont, CA (US)

( * ) Notice: Subject to any disclaimer, the term of this patent is extended or adjusted under 35 U.S.C. 154(b) by 710 days.

(21) Appl. No.: 10/716,176

(22) Filed: Nov. 17, 2003

(65) Prior Publication Data
US 2005/0051706 A1 Mar. 10, 2005

Related U.S. Application Data

(60) Provisional application No. 60/427,664, filed on Nov. 18, 2002, provisional application No. 60/436,855, filed on Dec. 26, 2002, provisional application No. 60/439,917, filed on Jan. 13, 2003, provisional application No. 60/451,177, filed on Feb. 27, 2003, provisional application No. 60/456,870, filed on Mar. 21, 2003, provisional application No. 60/501,599, filed on Sep. 9, 2003.

(51) Int. Cl.
*G01J 1/00* (2006.01)

(52) U.S. Cl. ............................ 356/213; 356/218; 435/5; 250/458.1

(58) Field of Classification Search ................ 356/213, 356/218, 319, 326; 435/5, 6, 7; 250/458.1, 250/459.1
See application file for complete search history.

(56) References Cited

U.S. PATENT DOCUMENTS

| | | | |
|---|---|---|---|
| 4,981,333 A | 1/1991 | Hayes | |
| 5,068,542 A | 11/1991 | Ando et al. | |
| 5,399,866 A | 3/1995 | Feldman et al. | |
| 5,981,207 A | 11/1999 | Burbaum et al. | |
| 5,998,580 A | 12/1999 | Fay et al. | |
| 6,215,549 B1 | 4/2001 | Suzuki et al. | |
| 6,225,625 B1 | 5/2001 | Pirrung et al. | |
| 6,252,236 B1 | 6/2001 | Trulson et al. | |
| 6,294,327 B1 | 9/2001 | Walton et al. | |

OTHER PUBLICATIONS

AB-Manufacturing, Inc. "AB-M Series 60 Exposure Systems" product literature, 1 page.

Adams et al. (1993) "Controlling Cell Chemistry with Caged Compounds" *Ann. Rev. Physiol.* 55:755-84.

Amit, B., et al. (1976) "Light-sensitive Amides. The photosolvolysis of substituted 1-acyl-7-nitroindolines" *J. Am. Chem. Soc.* 98(3):843-44.

Cairn Research Ltd. "Flash Photolysis," World Wide Web at: http://www.cairnweb.com/systems/flash.html, 2 pages, Mar. 3, 2001.

(Continued)

*Primary Examiner*—Hoa Q. Pham
(74) *Attorney, Agent, or Firm*—Monica Elrod-Erickson; Quine Intellectual Property Law Group, P.C.

(57) ABSTRACT

Uncaging devices that can be used to uncage photoactivatable caged components are provided. Consistent, uniform and/or high throughput processing of reactions and assays that include caged components is provided. Masked multi-well plates that can be used for uncaging photoactivatable caged components are provided. Methods and apparatus for initiating assays involving caged components are provided.

71 Claims, 20 Drawing Sheets

OTHER PUBLICATIONS

Denk, W., et al. (1990) "Two-photon laser scanning fluorescence microscopy." *Science* 248 (4951): 73-76.

Fodor, S.P., et al. (1991) "Light-directed, spatially addressable parallel chemical synthesis," *Science*, 251(4995): 767-73.

Fryer Company, Inc. Newsletter, *Focus on Fryer*, vol. 1, Issue 2, Summer 2000.

Haugland, R.P. (2002) "Caging Groups and Their Photolysis" *Handbook of Fluorescent Probes and Research Products*, Molecular Probes Inc., Eugene, OR, Section 17.1, pp. 709-710.

Mineralogical Research Co. "Mineralight and Blak-Ray Ultraviolet Lamps for Mineral, Gem and Lapidary Applications," World Wide Web at http://www.minresco.com/uvlamps/uvp/handlamp.htm, 4 pages; Oct. 20, 2002. Copyright by UVP, Inc.

OAI "UV Exposure Components" Product literature, 2 pages, copyright 2003 by OAI.

Oriel Instruments "Flood Exposures Sources" Product Literature, 1 page.

Photonic Instruments, Inc. "MicroPoint Laser System for Bio-Medical and Life Sciences," World Wide Web at http://www.photonic-instruments.com/micro-life.html, 2 pages, Aug. 4, 2002.

Photonic Instruments, Inc. "MicroPoint Flash Photolysis/Pulsed Fluorescence/Video Stroboscope Microscopy System," World Wide Web at: http://www.photonic-instruments.com/flash-lamp.html, 3 pages, Jun. 9, 2002.

Prairie Technologies, Inc. "Integrated Laser Imaging and Electrical Recording, Software Overview." On the World Wide Web at: http://www.prairie-technologies.com/PDF/intg-img-elec.pdf, 18 pages, Jun. 10, 2003. Copyright Prairie Technologies, Inc.

Prairie Technologies, Inc. "The Prairie Uncager-Data Sheet" On the World Wide Web at: http://www.prairie-technologies.com/PDF/Uncager.pdf, 2 pages, Apr. 4, 2003. Copyright Prairie Technologies, Inc.

Prairie Technologies, Inc. "Single Path Photolysis Head-Data Sheet" On the World Wide Web at: http://www.prairie-technologies.com/PDF/singlepathphotolysis.pdf, 1 page, Jun. 10, 2003.

Prairie Technologies, Inc. "Fiber Optic Laser Launches-Data Sheet" On the World Wide Web at: http://www.prairie-technologies.com/PDF/laserlaunch.pdf, 1 page, Apr. 3, 2004.

Rapp OptoElectronic "Introduction to our Flash Lamp Systems" World Wide Web at: http://rapp-opto.com/flashlamps.htm 1 page, Jun. 4, 2002.

Rapp OptoElectronic "Rapp OptoElectronic Flash Unit," World Wide Web at: http://www.asiimaging.com/rapp_flash.html, 2 pages, Jan. 8, 2004, Copyright ASI, Inc.

Rapp, G., Guth, K. (1988) "A low cost high intensity flash device for photolysis experiments" *Pflugers Arch*. 411:200-3.

Rapp G. (1998) "Flash lamp-based irradiation of caged compounds" In: *Methods in Enzymology*, vol. 291, G. Marriott (ed.), 202-222.

Sheehan, J. C., et al. (1971) "The photolysis of methoxy- substituted benzoin esters. A photosensitive protecting group for carboxylic acids." *J. Am. Chem. Soc.* 93(26):7222-28.

Spectroline "Hand-Hled UV Lamps" World Wide web at: http://www.spectroline.com/lab_lamps_hand.html, 4 pages, Mar. 31, 2001, Copyright Spectronics Corporation.

Southern New England Ultra Violet Company "P-9710-1 Optometer Specifications", World Wide Web at http://www.rayonet.org/word%20pages/lightmeters1.pdf p. 1 of 1, Oct. 16, 2003.

Southern New England Ultra Violet Company "X1 1 Optometer Specifications", World Wide Web at http://www.rayonet.org/word%20pages/lightmeters2.pdf, p. 1 of 1, Oct. 16, 2003.

Southern New England Ultra Company "Reactors", World Wide Web at http://www.rayonet.org/reactor.htm, 2 pages, Dec. 3, 2003.

Tamarack Scientific Co., Inc. "Collimated UV Light Sources" World Wide Web at: http://tamsci.com/products/uvlighsrc.html, p. 1 of 1, Aug. 30, 2002.

Walker, J. W., et. al. (1989) "Synthesis and properties of caged nucleotides" *Methods in Enzymol.* 172:288-301.

Walker, J. W., Trentham, D. R. (1988) "Caged phenylephrine: synthesis and photochemical properties" *Biophys. J.* 53:596a.

Watai, Y.,et al. (2001) "Regulation of nuclear import by light-induced activation of caged nuclear localization signal in living cells" *FEBS Letters* 488: 39-44.

Wootton, J. F., Trentham, D. R. (1989). ""Caged" compounds to probe the dynamics of cellular processes: synthesis and properties of some novel photosensitive P-2-nitrobenzyl esters of nucleotides" *Photochemical Probes in Biochemistry* P.E. Nielsen (ed) 272:277-96.

UNCAGING DEVICE

CROSS REFERENCE TO RELATED APPLICATIONS

This application is a non-provisional utility patent application claiming priority to and benefit of the following prior provisional patent applications: U.S. Ser. No. 60/427,664, filed Nov. 18, 2002, entitled "Photo Activated Sensors, Regulators and Compounds" by Nguyen and McMaster, U.S. Ser. No. 60/436,855, filed Dec. 26, 2002, entitled "Caged Sensors, Regulators and Compounds and Uses Thereof" by Nguyen and McMaster, U.S. Ser. No. 60/439,917, filed Jan. 13, 2003, entitled "Caged Sensors, Regulators and Compounds and Uses Thereof" by Nguyen and McMaster, U.S. Ser. No. 60/451,177, filed Feb. 27, 2003, entitled "Caged Sensors, Regulators and Compounds and Uses Thereof" by Nguyen et al., U.S. Ser. No. 60/456,870, filed Mar. 21, 2003, entitled "Caged Sensors, Regulators and Compounds and Uses Thereof" by Nguyen et al., and U.S. Ser. No. 60/501,599, filed Sep. 9, 2003, entitled "Caged Sensors, Regulators and Compounds and Uses Thereof" by Nguyen et al., each of which is incorporated herein by reference in its entirety for all purposes.

FIELD OF THE INVENTION

The invention is in the field of uncaging devices, namely, devices that can be used to uncage caged components. Masked multiwell plates and methods of initiating assays that include caged components are also described.

BACKGROUND OF THE INVENTION

A photolabile caged compound is a compound whose activity is inhibited, blocked or limited by the presence of one or more photolabile caging groups covalently associated with the compound. Exposure to light of an appropriate wavelength cleaves the caging group(s) from the compound, restoring its activity. A number of photolabile caged compounds have been (and are being) developed, including, for example, photolabile caged nucleotides, neurotransmitters, second messengers, and fluorescent dyes. Such photolabile caged compounds have been used, e.g., to examine various signaling pathways. However, the utility of such photolabile caged compounds (and other photoactivatable compounds) has been limited by lack of a convenient technology for uncaging the compounds reproducibly, uniformly, and safely, across various formats.

Devices that adapt microscopes for uncaging samples on microscope slides exist and are commercially available, e.g., from Photonic Instruments, Inc. (MicroPoint™ flash photolysis system, www.photonic-instruments.com); Cairn Research Ltd. (xenon arc flash photolysis system, www.cairnweb.com); Rapp OptoElectronic (fiber optic flash photolysis system, www.rapp-opto.com); and Fryer Company, Inc. and Prairie Technologies, Inc. (fiber optic, UV, and laser photolysis systems; www.fryerco.com and www.prairie-technologies.com). However, these devices cannot uncage samples in multiwell plate, test tube, or other common laboratory formats. Devices such as xenon or mercury flash or ultraviolet (UV) lamps (e.g., Blak-Ray UV lamps from Spectronics Corporation, www.spectroline.com) can be used for uncaging, but the illumination provided by these devices (e.g., the optical energy density to which the sample is exposed) is typically not uniform or reproducible from use to use. In addition, such lamps typically have no safety features to prevent accidental exposure of a user to UV light, are not simple to use, and provide low energy light. Devices such as a RAYONET Photochemical Reactor (available from Southern N.E. Ultraviolet Co., Branford, Conn.) can be used for uncaging but, e.g., do not allow the wavelength or optical energy density to which the sample is exposed to be conveniently controlled. In U.S. Pat. No. 5,981,207 (Nov. 9, 1999), Burbaum et al. suggest that a microplate reader can be adjusted and used for uncaging, but the UV light produced by such readers typically has an inconveniently low optical power density.

The present invention provides uncaging devices that overcome the above noted and other difficulties. A complete understanding of the invention will be obtained upon review of the following.

SUMMARY OF THE INVENTION

This invention relates to uncaging of photoactivatable caged components. Uncaging devices and masked multiwell plates that can be used, e.g., for uncaging photoactivatable caged components are provided, as are related methods of initiating assays by uncaging photoactivatable caged components of the assays.

In a first aspect, the invention provides uncaging devices. One general class of embodiments provides an apparatus comprising a work area, an uncaging light source that directs uncaging light at the work area or a selected portion thereof, and an optical meter that monitors the uncaging light. In this class of embodiments, the optical meter is positioned in a first plane that runs through the work area. Another general class of embodiments provides an apparatus comprising a work area, an uncaging light source that directs uncaging light at the work area or a selected portion thereof, a multiwell plate, and a plate holder. The plate holder is configured to accept the multiwell plate in a first fixed position, wherein the multiwell plate in the first fixed position occupies the work area. The multiwell plate comprises a photoactivatable caged component, and exposure to the uncaging light results in uncaging of the caged component. The uncaging light typically has an optical power density greater than 100 $\mu W/cm^2$ at one or more wavelengths between about 100 nm and about 400 nm. Yet another general class of embodiments provides an apparatus comprising a work area, an uncaging light source that directs uncaging light at the work area or a selected portion thereof, and an exposure controller. The exposure controller controls optical energy density of the uncaging light to which the work area or the selected portion thereof is exposed, whereby the work area is exposed to a desired optical energy density selected by a user of the device. In this class of embodiments, optical power density of the uncaging light is substantially uniform over the entire work area.

Another aspect of the invention provides masked multiwell plates. Thus, one general class of embodiments provides a masked multiwell plate that comprises a multiwell plate and a mask. The mask alters optical power density of uncaging light impinging on at least a first portion of the multiwell plate (e.g., on at least one well or portion of a well). In some embodiments, the mask inhibits or prevents the uncaging light from impinging on at least the first portion of the multiwell plate and permits the uncaging light to impinge on at least a second portion of the multiwell plate. In other embodiments, the mask decreases the optical power density of the uncaging light impinging on the first portion of the multiwell plate, but does not completely block transmission of the uncaging light.

Yet another aspect of the invention provides methods, e.g., methods of initiating assays comprising photoactivatable caged components. One general class of embodiments provides methods of initiating an assay within a reaction area. In the methods, at least one photoactivatable caged component of the assay is introduced into the reaction area, which has an area of at least about 50 mm². The reaction area is exposed to uncaging light, which exposure results in uncaging of the caged component. The optical power density of the uncaging light is substantially uniform over the entire reaction area.

DEFINITIONS

Figure 1:
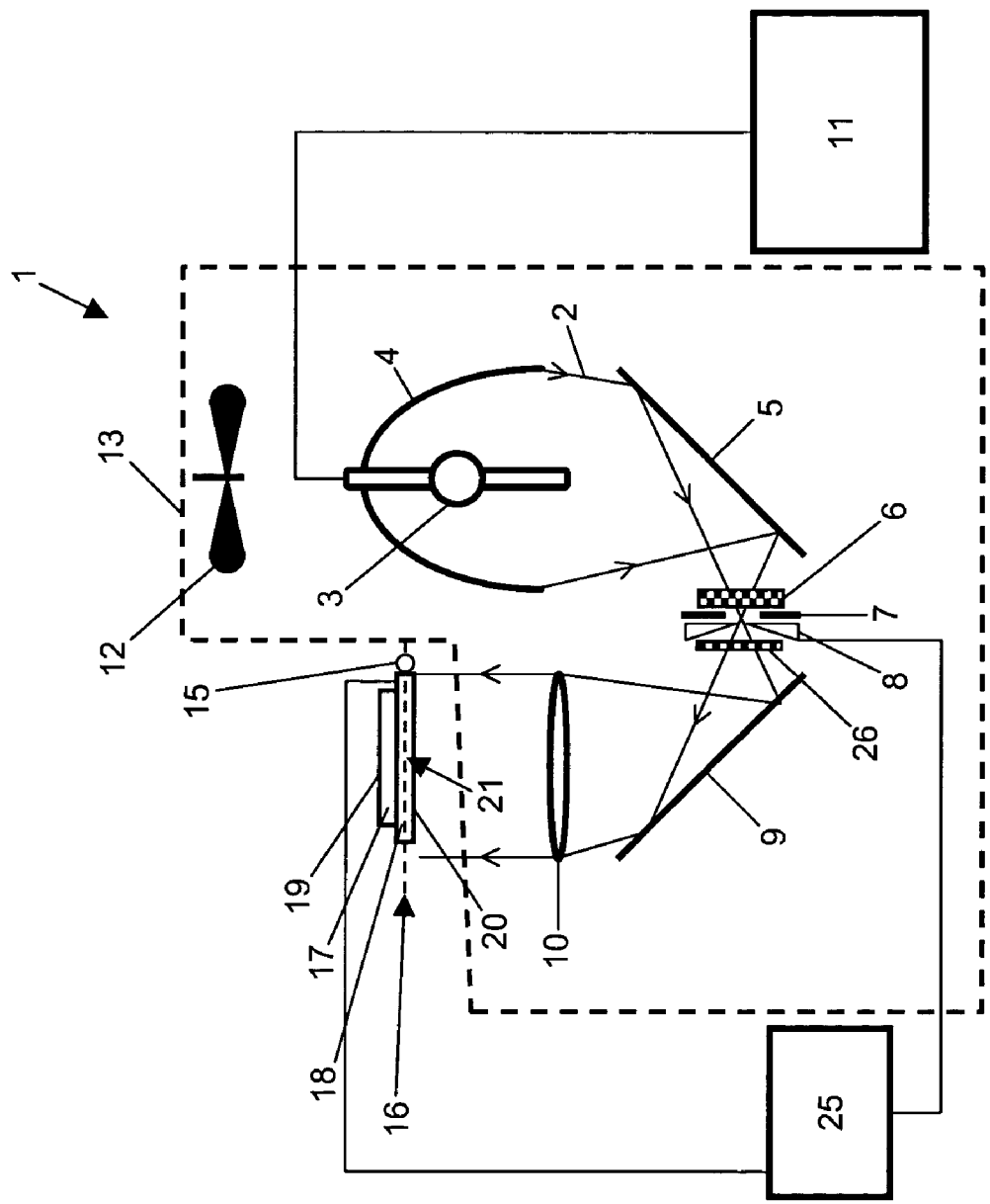
FIG. 1 schematically depicts an uncaging device.

Unless defined otherwise, all technical and scientific terms used herein have the same meaning as commonly understood by one of ordinary skill in the art to which the invention pertains. The following definitions supplement those in the art and are directed to the current application and are not to be imputed to any related or unrelated case, e.g., to any commonly owned patent or application. Although any methods and materials similar or equivalent to those described herein can be used in the practice for testing of the present invention, the preferred materials and methods are described herein. Accordingly, the terminology used herein is for the purpose of describing particular embodiments only, and is not intended to be limiting.

As used in this specification and the appended claims, the singular forms "a," "an" and "the" include plural referents unless the content clearly dictates otherwise. Thus, for example, reference to "a component" includes a plurality of components; reference to "a cell" includes mixtures of cells, and the like.

An "assay" is a reaction or set of reactions performed for the purpose of determining the presence, concentration, activity, and/or the like of a molecule (e.g., a biomolecule, e.g., a polypeptide, nucleic acid, lipid, or carbohydrate) or a complex of such molecules, as opposed to a reaction performed for the purpose of synthesizing or degrading a molecule. The activity of an enzyme can be "assayed", either qualitatively (e.g., to determine if the activity is present) or quantitatively (e.g., to determine kinetic and/or thermodynamic constants of the reaction). Similarly, an intermolecular association (e.g., a binding reaction between two molecules) can be "assayed", either qualitatively (e.g., to determine if the association occurs) or quantitatively (e.g., to determine kinetic and/or thermodynamic constants of the reaction, e.g., a dissociation constant). Concentration of a molecule can also be assayed.

A "caging group" is a moiety that can be employed to reversibly block, inhibit, or interfere with the activity (e.g., the biological activity) of a molecule (e.g., a polypeptide, a nucleic acid, a small molecule, a drug, etc.). The caging groups can, e.g., physically trap an active molecule inside a framework formed by the caging groups. Typically, however, one or more caging groups are associated (covalently or noncovalently) with the molecule but do not necessarily surround the molecule in a physical cage. For example, a single caging group covalently attached to an amino acid side chain required for the catalytic activity of an enzyme can block the activity of the enzyme; the enzyme would thus be caged even though not physically surrounded by the caging group. Caging groups can be, e.g., relatively small moieties such as carboxyl nitrobenzyl, 2-nitrobenzyl, nitroindoline, hydroxyphenacyl, DMNPE, or the like, or they can be, e.g., large bulky moieties such as a protein or a bead. Caging groups can be removed from a molecule, or their interference with the molecule's activity can be otherwise reversed or reduced, by exposure to an appropriate type of uncaging energy and/or exposure to an uncaging chemical, enzyme, or the like.

A "photoactivatable" or "photoactivated" caging group is a caging group whose blockage, inhibition of, or interference with the activity of a molecule with which the photoactivatable caging group is associated can be reversed or reduced by exposure to light of an appropriate wavelength ("uncaging light"). For example, exposure to uncaging light can disrupt a network of caging groups physically surrounding the molecule, reverse a noncovalent association with the molecule, trigger a conformational change that renders the molecule active even though still associated with the caging group, or cleave a photolabile covalent attachment to the molecule. A "photoactivatable caged component" or "photoactivatable caged compound" comprises at least one photoactivatable caging group.

A "photolabile" caging group is one whose covalent attachment to a molecule is reversed (cleaved) by exposure to light of an appropriate wavelength. The photolabile caging group can be, e.g., a relatively small moiety such as carboxyl nitrobenzyl, 2-nitrobenzyl, nitroindoline, hydroxyphenacyl, DMNPE, or the like, or it can be, e.g., a relatively bulky group (e.g., a macromolecule, a protein) covalently attached to the molecule by a photolabile linker (e.g., a polypeptide linker comprising a 2-nitrophenyl glycine residue). A "photolabile caged component" or "photolabile caged compound" comprises at least one photolabile caging group.

A "label" is a moiety that facilitates detection of a molecule. Common labels in the context of the present invention include fluorescent, luminescent, and/or colorimetric labels. Suitable labels include fluorescent nucleotides, enzymes, substrates, cofactors, inhibitors, fluorescent moieties, chemiluminescent moieties, magnetic particles, and/or the like. Patents teaching the use of such labels include U.S. Pat. Nos. 3,817,837; 3,850,752; 3,939,350; 3,996,345; 4,277,437; 4,275,149; and 4,366,241. Many labels are commercially available and can be used in the context of the invention.

The term "nucleic acid" encompasses any physical string of monomer units that can be corresponded to a string of nucleotides, including a polymer of nucleotides (e.g., a typical DNA or RNA polymer), PNAs, modified oligonucleotides (e.g., oligonucleotides comprising nucleotides that are not typical to biological RNA or DNA in solution, such as 2'-O-methylated oligonucleotides), and/or the like. A nucleic acid can be e.g., single-stranded or double-stranded. Unless otherwise indicated, a particular nucleic acid sequence of this invention encompasses complementary sequences, in addition to the sequence explicitly indicated. A nucleic acid (e.g., an oligonucleotide, a molecular beacon, an antisense nucleic acid, a nucleic acid molecular decoy, a nucleic acid binding sensor, an aptamer, a nucleic acid probe, or the like) of this invention is optionally nuclease resistant.

A "polypeptide" is a polymer comprising two or more amino acid residues (e.g., a peptide or a protein). The polymer can additionally comprise non-amino acid elements such as labels, quenchers, blocking groups, or the like and can optionally comprise modifications such as glycosylation or the like. The amino acid residues of the polypeptide can be natural or non-natural and can be unsubstituted, unmodified, substituted or modified.

A variety of additional terms are defined or otherwise characterized herein.

DETAILED DESCRIPTION

The invention features uncaging devices that can be used, e.g., to uncage photoactivatable caged compounds. Masked multiwell plates that can be used, e.g., with the uncaging devices form another feature of the invention, as do methods of initiating an assay by uncaging a photoactivatable caged component of the assay (e.g., using an uncaging device of the invention).

Uncaging Devices

One aspect of the invention provides uncaging devices. Thus, a first general class of embodiments provides an apparatus comprising a work area, an uncaging light source that directs uncaging light at the work area or a selected portion thereof, and an optical meter that monitors the uncaging light. In this class of embodiments, the optical meter is positioned in a first plane that runs through the work area. A second general class of embodiments provides an apparatus comprising a work area, an uncaging light source that directs uncaging light at the work area or a selected portion thereof, a multiwell plate, and a plate holder. The plate holder is configured to accept the multiwell plate in a first fixed position, wherein the multiwell plate in the first fixed position occupies the work area. The multiwell plate comprises a photoactivatable caged component, and exposure to the uncaging light results in uncaging of the caged component. The uncaging light typically has an optical power density greater than 100 $\mu W/cm^2$ (e.g., equal to or greater than about 300 $\mu W/cm^2$, 500 $\mu W/cm^2$, 700 $\mu W/cm^2$, or 900 $\mu W/cm^2$) at one or more wavelengths between about 100 nm and about 400 nm (the apparatus optionally also produces uncaging light with a wavelength greater than about 400 nm). A third general class of embodiments provides an apparatus comprising a work area, an uncaging light source that directs uncaging light at the work area or a selected portion thereof, and an exposure controller. The exposure controller controls optical energy density of the uncaging light to which the work area or the selected portion thereof is exposed, whereby the work area is exposed to a desired optical energy density selected by a user of the device. In this class of embodiments, optical power density of the uncaging light is substantially uniform over the entire work area.

FIG. 1 schematically illustrates an example uncaging device. Apparatus 1 includes an uncaging light source (lamp 3, e.g., a mercury arc lamp) that directs uncaging light (beam bounded by rays 2) at work area 21 (the region of the device in which components generally are uncaged) or a selected portion thereof. In this example embodiment, uncaging light generated by lamp 3 is collected and focused by parabolic reflector 4 onto optical homogenizer 6. Optical homogenizer 6 comprises two arrays of small lenses, the first of which splits and scrambles incoming light and the second of which recombines it, such that the output light is highly uniform. Iris 7 (e.g., a fixed iris) and shutter 8 are positioned near optical homogenizer 6. Collimating lens 10, positioned near work area 21, collimates the uncaging light. In this example, dichroic mirrors 5 and 9 are inserted in the optical path at 45° angles; these mirrors reflect light in the UV range but let light in the visible and infrared ranges pass through. Lamp 3 is connected to power supply 11. Cooling fan 12 keeps the temperature within optical unit 13 from rising above that tolerated by lamp 3.

Optical unit 13 can optionally be adapted from commercially available exposure systems or uniform UV light sources such as those used in the semiconductor industry, for example, those available from AB Manufacturing Inc. (Model 66-5), Optical Associates Inc. (Model LS30/7), Spectra-Physics' Oriel Division (Model 82530-1000), Taramack Scientific Inc. (Model PRX500-9), or Quintel Corp.

It will be evident that FIG. 1 presents a single example of possible configurations for the optical unit and that a number of variations are possible. For example, depending on the optical setup, any of a variety of light sources can be used, including, but not limited to, lamps (e.g., continuous or flash lamps) or lasers. As another example, a collimating mirror can be used instead of a collimating lens, or the uncaging light can be uncollimated. As yet another example, the light can be guided from the light source to the work area by lenses or a fiber optic bundle, for example, instead of by dichroic mirrors. A few example alternative optical setups are illustrated in FIGS. 15-17.

FIG. 15 Panel A schematically illustrates an example uncaging device in which one or more fiber optic bundles guide the uncaging light from the light source to the work area. Uncaging device 151 includes focusing optics 153 that direct uncaging light produced by lamp 152 (e.g., a mercury lamp) through shutter 154 and filter 155 to fiber optic bundle 156. The uncaging light passes through optional diffuser 157 and impinges on multiwell plate 158, which occupies the work area. As noted, one or more bundles can be used to illuminate one or more portions of the work area (e.g., one or more wells of a multiwell plate occupying the work area), sequentially or simultaneously. For example, Panel B illustrates use of a single bundle to illuminate a single well of a multiwell plate (filled circle); the other wells (open circles) can be illuminated, e.g., by scanning the plate in two-dimensional steps (directions of movement indicated by open arrows), by translating the plate and/or the bundle. Panel C illustrates use of a multi-bundle to illuminate a column of wells of a multiwell plate (filled circles); the other wells (open circles) can be illuminated, e.g., by scanning the plate in one-dimensional steps (direction of movement indicated by open arrow). Panel D illustrates use of a line-bundle (black line) to illuminate a portion of a column of wells of a multiwell plate; the remainder of the plate can be illuminated, e.g., by scanning the plate in a one-dimensional continuous scan (direction of movement indicated by open arrow).

Figure 16B:
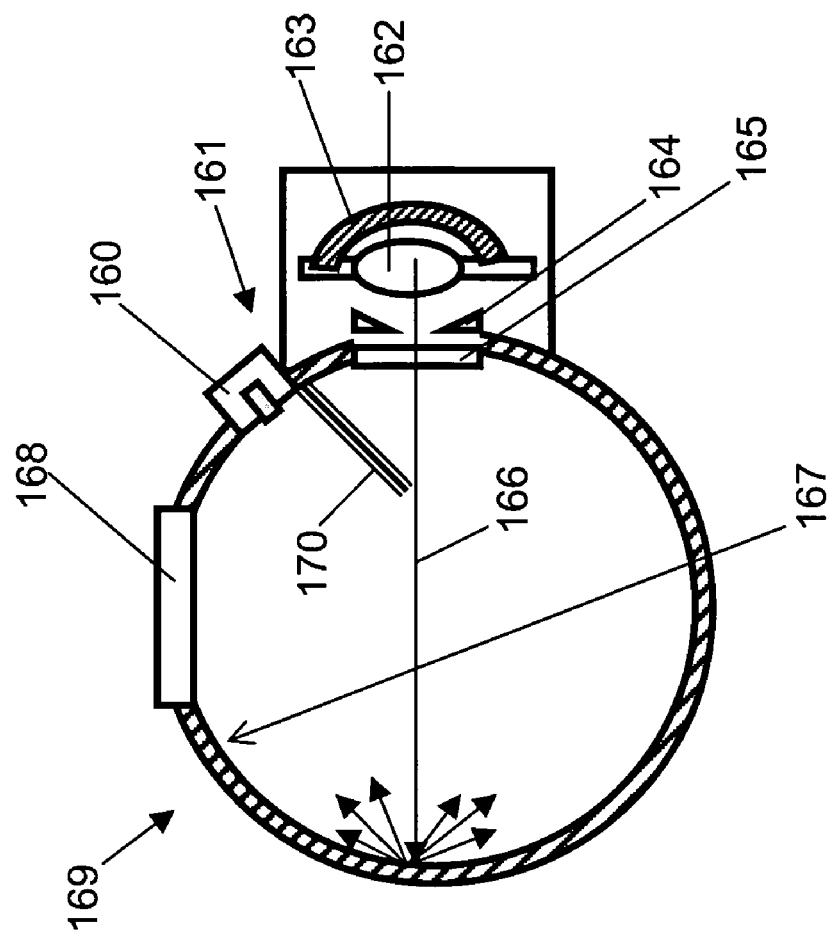
FIG. 16 Panel A depicts an integrating sphere. Panel B schematically illustrates an uncaging device comprising an integrating sphere.
Figure 16A:
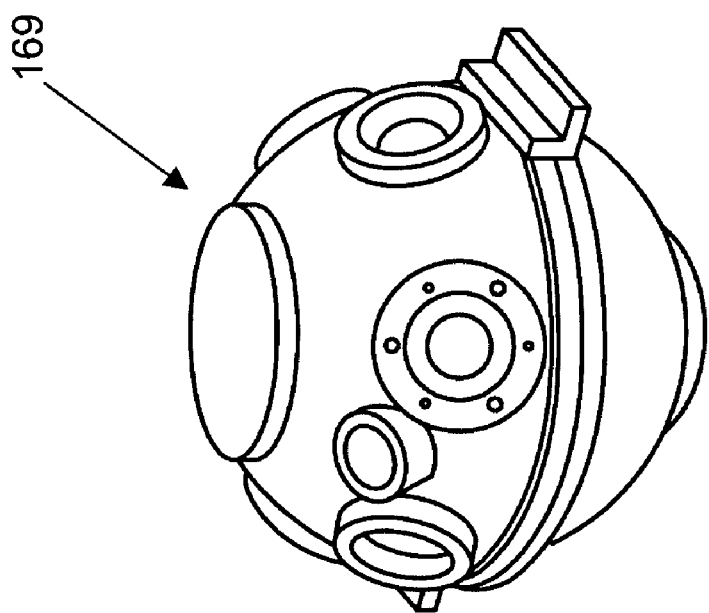

FIG. 16 Panels A and B schematically illustrate an example uncaging device comprising an integrating sphere. Uncaging device 161 includes focusing optics 163 that direct uncaging light produced by light source 162 along a path indicated by ray 166, through shutter 164 and filter 165. The uncaging light is reflected by the highly diffusive coating on inside surface 167 of integrating sphere 169 and impinges on multiwell plate 168, which occupies the work area. Optical meter 160 monitors the uncaging light. Blocker 170 increases uniformity of the uncaging light by preventing light from traveling directly from light source 162 to the work area.

Figures 17A, 17B:
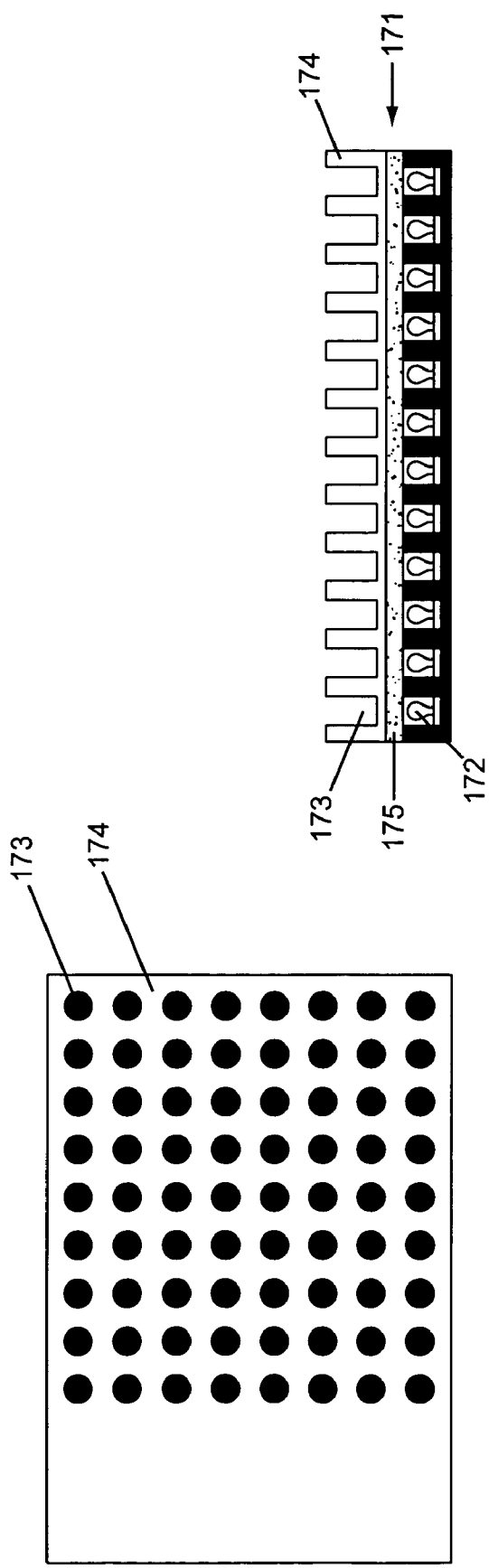
FIG. 17 schematically depicts an uncaging device. Panel A is a top view and Panel B is a cross-section of the uncaging device.

FIG. 17 Panels A and B schematically illustrate an example uncaging device in which one or more LEDs serve as the uncaging light source. For example, in uncaging device 171, an array of twelve columns and eight rows of UV LEDs 172 illuminates wells 173 of 96 well plate 174. The uncaging light produced by each LED 172 passes through diffuser 175 (which can be a single structure, as illustrated, or a number of smaller structures, e.g., one per well) before impinging on wells 173.

In some embodiments, at least one reaction region occupies the work area (e.g., a single reaction region or a plurality of reaction regions). The reaction region can comprise, for example, a well of a multiwell plate (e.g., well 42 of plate 17 in FIG. 3 Panel D), a sample tube, a channel of a microfluidic chip, a capillary, a spot on a two-dimensional array, a spot on a three-dimensional array, a slide, or a flow region of a flow cytometer.

In the example embodiment illustrated in FIG. 1, uncaging device 1 also includes plate holder 18 (FIG. 3 Panels A, B and D). Plate holder 18 accepts multiwell plate 17 in a first fixed position, with multiwell plate 17 occupying work area 21. As illustrated, the uncaging light passes through aperture 22 in plate holder 18 and impinges on bottom surface 20 of multiwell plate 17. Alternatively or in addition, in other embodiments, the uncaging light can impinge on top surface 19 of multiwell plate 17. It will be evident that when a slide, microfluidic chip, capillary, sample tube, or other reaction region occupies the work area, the uncaging light can impinge on its bottom, top, and/or side, as desired. Multiwell plate 17 can be, for example, any of a variety of commercially available multiwell plates (sometimes called "microtiter" plates), e.g., a commercially available 12, 24, 48, 96, 384, 1536, or even 3456 or 9600 well plate, or a custom-designed multiwell plate with any number of wells. In embodiments in which the uncaging light impinges on the bottom surface of the multiwell plate, the bottom of each well of the multiwell plate preferably does not significantly interfere with transmission of the uncaging light. The multiwell plate is optionally a black well plate, in which light is not transmitted between adjacent wells of the plate.

In certain embodiments, the apparatus also includes an optical meter that monitors the uncaging light (e.g., an optical power density meter, an optical power meter, an optical energy density meter, or an optical energy meter). As illustrated in FIG. 1, optical meter 15 is preferably located in first plane 16 that runs through work area 21; in this configuration, optical meter 15 directly reads the optical power, optical power density, optical energy, optical energy density, or the like, of the uncaging light at the work area. Alternatively, optical meter 15 can be positioned out of first plane 16 so that the optical power, optical power density, optical energy, optical energy density, or the like, read by the meter is proportional, not equal, to that at the work area. First plane 16 can, but need not be, perpendicular to the path of the uncaging light. Typically, when at least one reaction region is occupying the work area, the first plane runs through the reaction region(s). For example, in the embodiment illustrated in FIG. 1, first plane 16 runs through the wells of multiwell plate 17. As illustrated, first plane 16 is parallel to top surface 19 and bottom surface 20 of multiwell plate 17.

The entirety of work area 21 can be illuminated by the uncaging light, or, if desired a selected portion of the work area can be illuminated (e.g., by focusing the uncaging light on the selected portion of the work area, preventing the uncaging light from impinging on other portions of the work area, or the like). The work area (or the selected portion thereof) can be of essentially any desired size. For example, the area of the work area or the selected portion thereof can be from about the cross-sectional area of a single cell to the area of a multiwell plate, or even larger; thus, the area of the work area or the selected portion thereof is optionally greater than 25 $\mu m^2$, greater than 0.01 $mm^2$, greater than 1 $mm^2$, greater than 100 $mm^2$, greater than 10 $cm^2$, greater than 100 $cm^2$, greater than 500 $cm^2$, or even greater than 1000 $cm^2$. Similarly, the area of the work area or the selected portion thereof can be about the area of a single well (or a portion of a well) of a multiwell plate, a single spot on an array, or a single cell, for example; thus, the area of the work area or the selected portion thereof is optionally less than 3 $cm^2$, less than 100 $mm^2$, less than 10 $mm^2$, less than 1.5 mm², less than 0.1 mm², less than 0.25 mm², less than 2500 µm², or less than 50 µm². When a plurality of selected portions of the work area are illuminated simultaneously (or sequentially), adjacent portions are optionally separated by a distance of less than about 10 mm, less than about 5 mm, less than about 1 mm, less than about 500 µm, less than about 100 µm, less than about 50 µm, less than about 20 µm, or even less than about 10 µm.

As is known in art, different photoactivatable caging groups have different optimal wavelengths of uncaging light. Thus, in some embodiments, the uncaging light has a wavelength selected by user of the apparatus (e.g., from a continuous spectrum or from a set of predefined distinct wavelengths). In other embodiments, the wavelength of the uncaging light is selected during manufacture of the apparatus.

The uncaging light can have essentially any wavelength (e.g., the uncaging light can have a wavelength between about 10 nm and about 1000 nm, e.g., between about 60 and about 1000 nm, e.g., between about 300 and about 700 nm). A large number of caging groups are removable by UV light. Thus, in one class of embodiments, the uncaging light has a wavelength in the UV range (e.g., a wavelength between about 10 nm and about 400 nm, e.g., between about 300 nm and about 400 nm). In one class of example embodiments, the uncaging light has a wavelength distribution centered at 365 nm.

In the example embodiment illustrated in FIG. 1, the wavelength of the uncaging light is determined by filter 26, positioned near shutter 8. (One alternative filter position, after collimating lens 10, is shown for filter 36 in FIG. 2.) The filter can be, e.g., permanently fixed in position, removable for replacement with a different filter that permits passage of a different wavelength light, part of a rotatable filter wheel, or the like.

In preferred embodiments, optical power density of the uncaging light is substantially uniform over the entire work area. Uniformity of the uncaging light can be defined as Uniformity=+/−(max−min)/(max+min), where max is the maximum optical power density read within the work area and min is the minimum optical power density read within the work area. Thus, for example, uncaging light with substantially uniform optical power density can have a uniformity less than about ±15%, less than about ±10%, less than about ±5%, less than about ±3%, less than about ±1.5%, or even less than about ±1% over the entire work area.

Optical power density of the uncaging light can be essentially any value useful for uncaging a caged component of interest. Typically, the optical power density of the uncaging light is greater than about 1 mW/cm² (e.g., greater than about 5 mW/cm², 10 mW/cm², 15 mW/cm², 20 mW/cm², 30 mW/cm², or more) and less than about 50,000 mW/cm² (e.g., less than about 20,000 mW/cm², 10,000 mW/cm², 5,000 mW/cm², or less).

In some embodiments, the uncaging device further comprises an exposure controller that controls optical energy density of the uncaging light to which the work area (or the selected portion thereof) is exposed. Typically, the exposure controller controls the optical energy density of the uncaging light by controlling optical power density of the uncaging light and/or an exposure time (an amount of time to which the work area or the selected portion thereof is exposed to the uncaging light). It is worth noting that the optical energy density is equal to the product of the optical power density and the exposure time.

In the embodiment illustrated in FIG. 1, for example, apparatus 1 includes exposure controller 25, which controls whether shutter 8 is open or closed. Exposure controller 25 can accept an input from a user of the apparatus, which input indicates a desired exposure time (e.g., the user can input the desired exposure time by means of at least one dial, keypad, graphical user interface, or the like). Exposure controller 25 then opens shutter 8 for the desired amount of time. Similarly, exposure controller 25 can accept an input from a user of the apparatus, which input indicates a desired optical energy density of uncaging light to which work area 21 is to be exposed (e.g., the desired optical energy density can be selected by the user to partially or completely uncage a caged component occupying work area 21).

As illustrated in FIG. 1, exposure controller 25 can accept a signal from optical meter 15. Exposure controller 25 optionally uses the signal from optical meter 15 to adjust the exposure time to achieve the desired optical energy density. For example, optical meter 15 can be an optical energy density meter. When the user inputs a desired optical energy density, exposure controller 25 opens shutter 8. The optical energy density meter reads the optical energy density of the uncaging light impinging on it (which the same as the optical energy density of the uncaging light impinging on work area 21, since optical meter 15 is located in first plane 16 with work area 21). When the desired optical energy density has been achieved, optical meter 15 signals exposure controller 25 which closes shutter 8. As another example, optical meter 15 can be an optical power density meter. When the user inputs a desired optical energy density, exposure controller 25 opens shutter 8. The optical power density meter reads the optical power density of the uncaging light impinging on it (which the same as the optical power density of the uncaging light impinging on the work area, since optical meter 15 is located in first plane 16 with work area 21). Optical meter 15 signals exposure controller 25, which calculates an appropriate exposure time to produce the desired optical energy density given the optical power density measured by optical meter 15. Exposure controller 25 closes shutter 8 after the calculated exposure time has elapsed.

In a preferred class of embodiments, an actual optical energy density to which the work area or the selected portion thereof is exposed is substantially equal to the desired optical energy density. For example, the actual optical energy density preferably varies from the desired optical energy density by less than 10%, less than 5%, or less than 3%.

In some embodiments, the apparatus also includes a mask that alters optical power density of the uncaging light impinging on at least a first portion of the work area. For example, the mask can prevent the uncaging light from impinging on at least the first portion of the work area and permit the uncaging light to impinge on at least a second portion of the work area. Alternatively, the mask can decrease the optical power density of the uncaging light impinging on the first portion of the work area without completely blocking the uncaging light. As will be evident, altering the optical power density of the uncaging light impinging on the first portion of the work area alters the optical power density of the uncaging light impinging on anything occupying the work area. Thus, in one class of embodiments, the uncaging device comprises a plate holder that is configured to accept a mask, the mask altering optical power density of the uncaging light impinging on at least a first portion of the multiwell plate. As noted, the mask can reduce the optical power density of the uncaging light (or completely block the uncaging light) impinging on one or more wells (or portions of wells) of the multiwell plate. For example, in the embodiment illustrated in FIG. 3 Panels A-D, plate holder 18 is configured to accept mask 40. Mask 40 prevents the uncaging light from impinging on the first portion (wells 43) of multiwell plate 17. Apertures 41 in mask 40 permit the uncaging light to impinge on second portion (wells 42) of plate 17.

In a related uncaging device, instead of being occupied by a multiwell plate, the plate holder is occupied by an adapter configured to accept one or more slides (e.g., microscope slides, microfluidic chips, microarrays, and/or the like). The slides are thus positioned in the work area, where a caged component on the slides can be uncaged.

Figure 4:
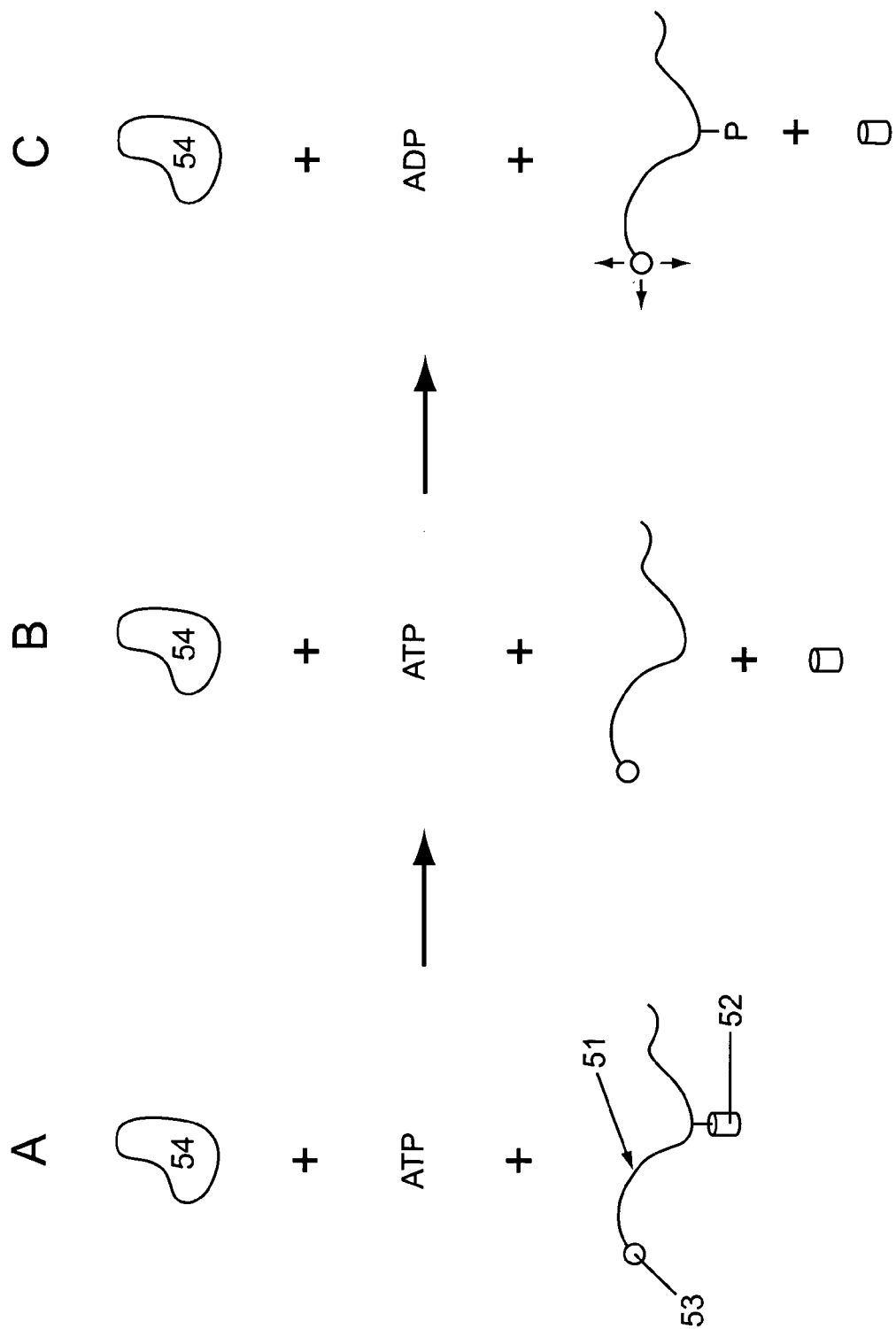
FIG. 4 schematically depicts a kinase assay employing a photoactivatable caged kinase sensor.

In embodiments in which at least one reaction region occupies work area 21, the reaction region (e.g., well 42) optionally comprises a photoactivatable (e.g., a photolabile) caged component (e.g., one or more photoactivatable components). Exposure to the uncaging light results in uncaging of the caged component. For example, FIG. 4 illustrates caged kinase sensor 51, which includes a kinase substrate, fluorescent label 53, and photolabile caging group 52 (Panel A). Exposure to uncaging light results in uncaging of the caged sensor (Panel B), which is then phosphorylated by kinase 54. Label 53 emits a more intense signal in the phosphorylated sensor (Panel C) than in the unphosphorylated sensor. The photoactivatable caged component can be a component of essentially any reaction, assay, sample, or the like. The photoactivatable caged component is optionally located inside a cell. The caged component can be essentially any caged compound, molecule, ion, complex, or the like. Caged components include, but are not limited to, caged polypeptides, caged nucleic acids, caged lipids, caged carbohydrates, caged small molecules, and caged metal ions; for example, a caged sensor (e.g., an enzyme or binding sensor), a caged nucleic acid probe, a caged modulator, a caged interfering RNA, a caged RNAi-based sensor, a caged antisense nucleic acid, a caged ribozyme, a caged biomolecular analog, a caged transcription factor, a caged molecular decoy, a caged antibody, a caged aptamer, a caged nucleotide (e.g., a caged nucleoside triphosphate or caged cAMP), a caged chelating agent, a caged fluorescent dye, a caged second messenger, or a caged neurotransmitter. See, e.g., U.S. patent application Ser. No. 60/501,599, filed Sep. 9, 2003, entitled "Caged sensors, regulators and compounds and uses thereof" by Nguyen et al.; U.S. patent application Ser. No. 60/484,785, filed Jul. 3, 2003, entitled "RNAi-based sensors and methods of use thereof" by Nguyen and McMaster; Haughland (2003) *Handbook of Fluorescent Probes and Research Products* Ninth Edition or the current Web Edition, available from Molecular Probes, Inc.; and Shigeri et al. (2001) "Synthesis and application of caged peptides and proteins" Pharmacology & Therapeutics 91:85-92). A number of caged compounds, including for example caged nucleotides, caged Ca2+, caged chelating agents, caged neurotransmitters, and caged luciferin, are commercially available, e.g., from Molecular Probes, Inc. (www.molecularprobes.com). In embodiments in which the reaction region comprises a plurality of caged components, the distinct caged components are optionally uncaged under distinct conditions (e.g., exposure to distinct wavelengths, optical power densities, and/or optical energy densities of uncaging light).

Figure 2:
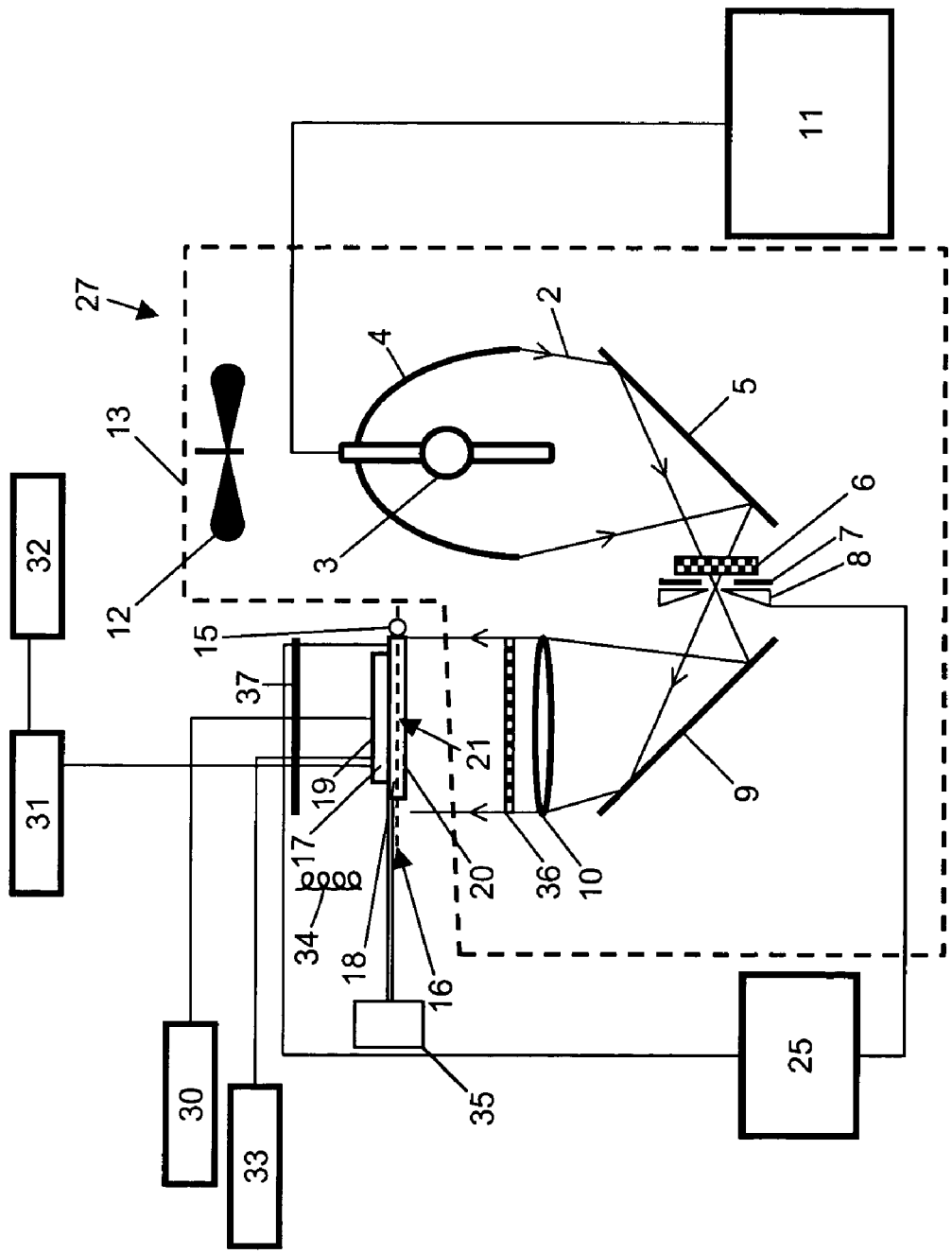
FIG. 2 schematically depicts an uncaging device.
Figure 3A:
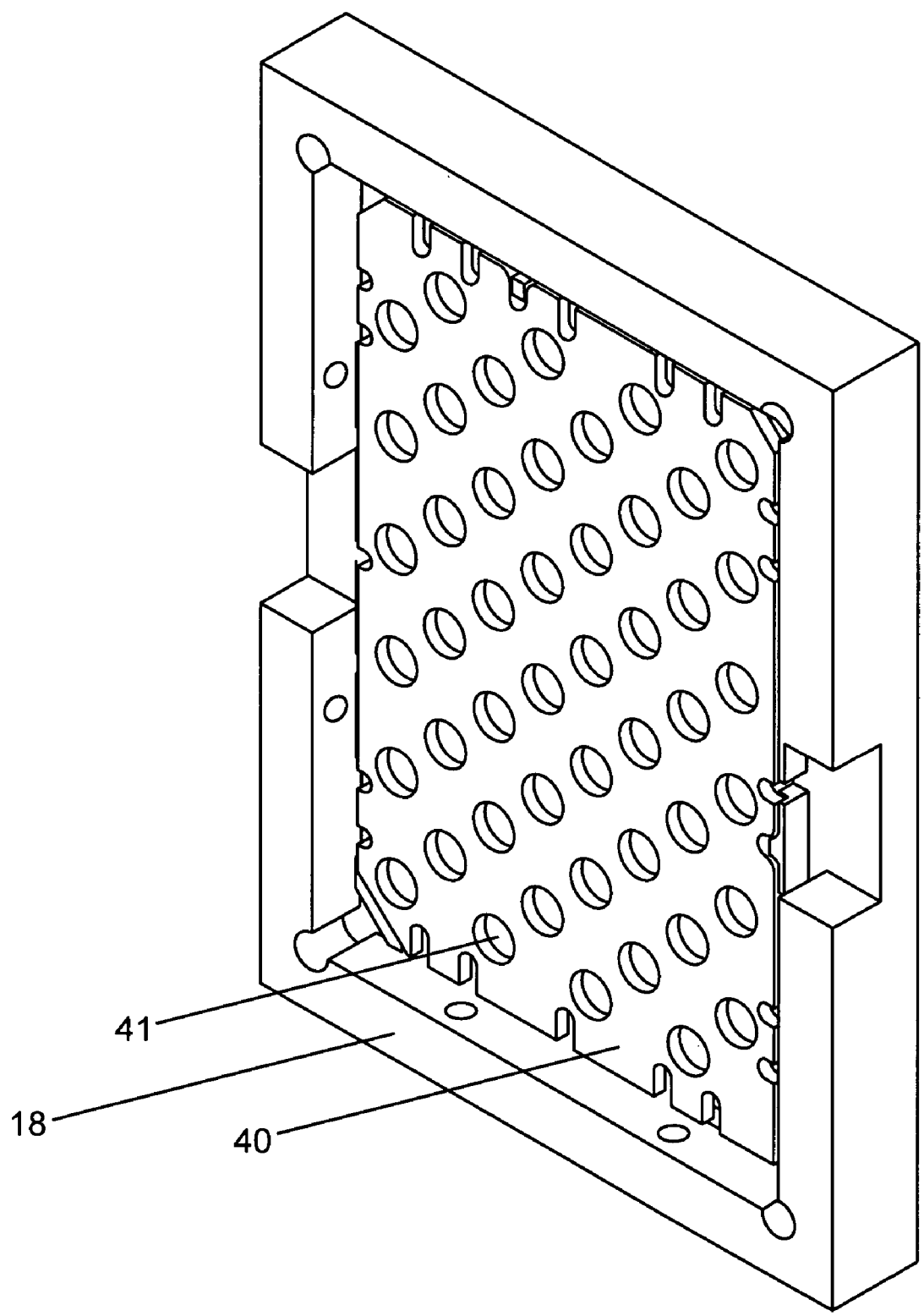
FIG. 3 Panel A is an isometric view of a plate holder and mask. Panel B is an isometric view of a plate holder. Panel C is an isometric view of a mask. Panel D is a cross-section of a plate holder containing a mask and a multiwell plate.
Figure 3B:
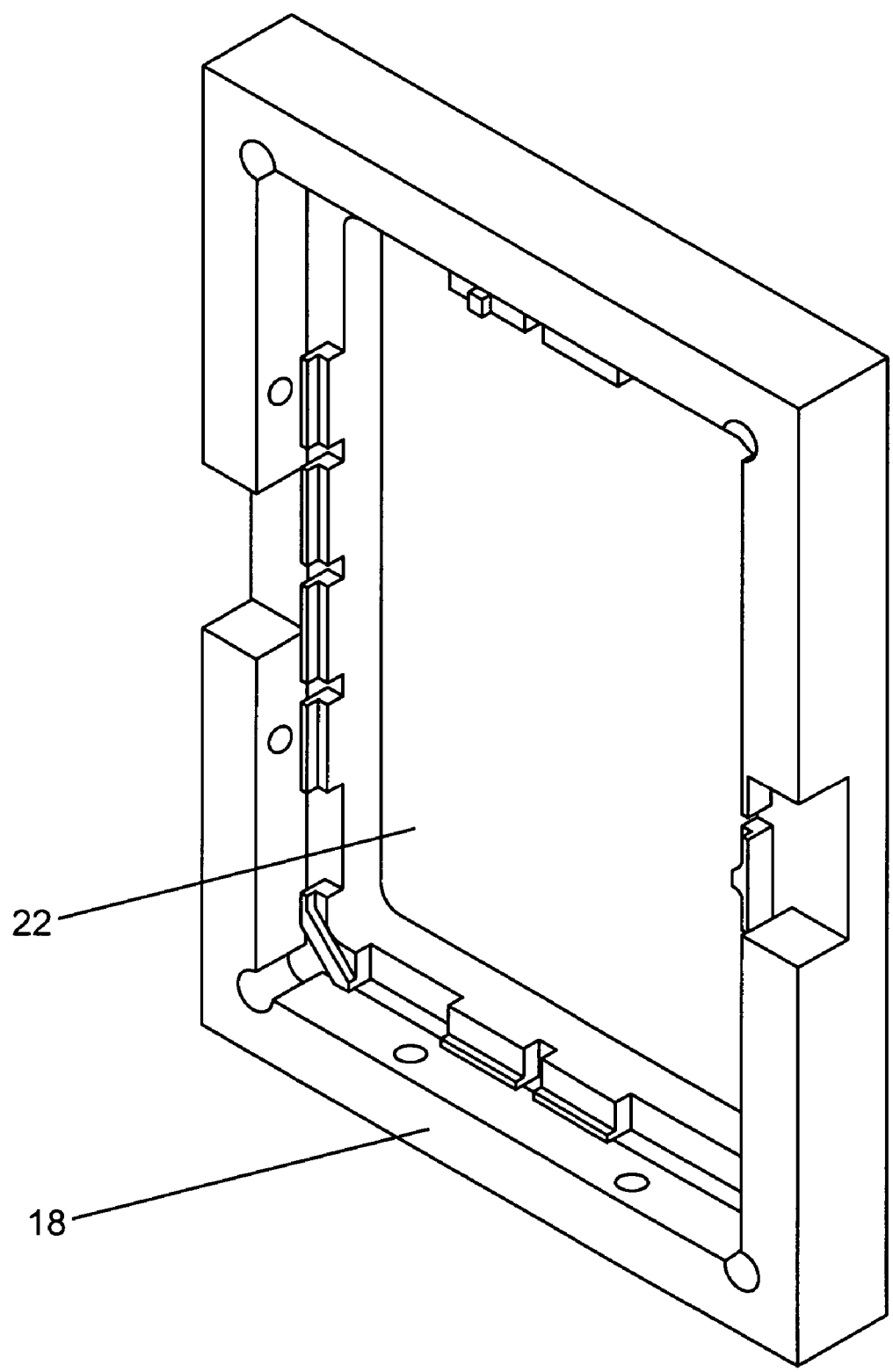
Figure 3C:
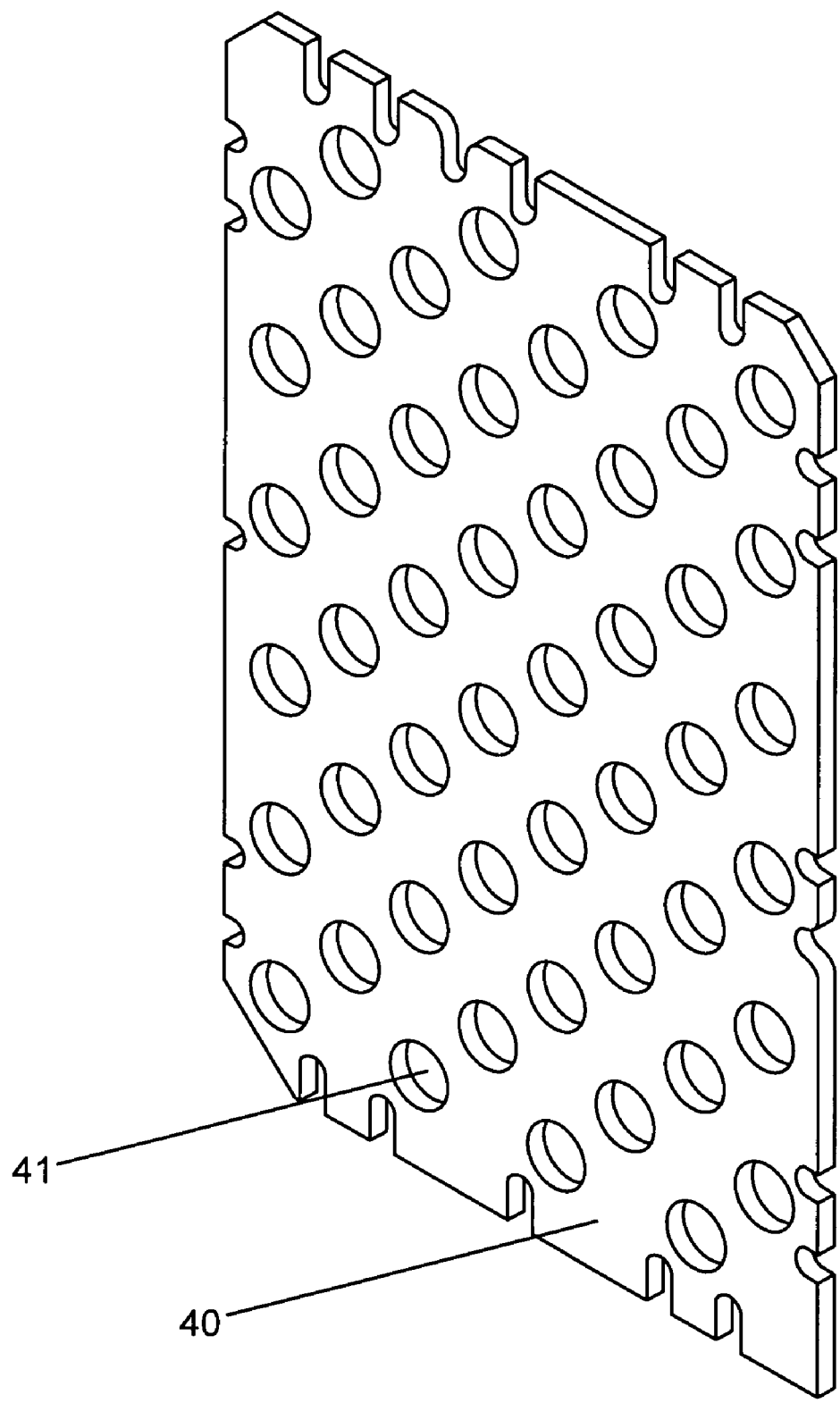
Figure 3D:
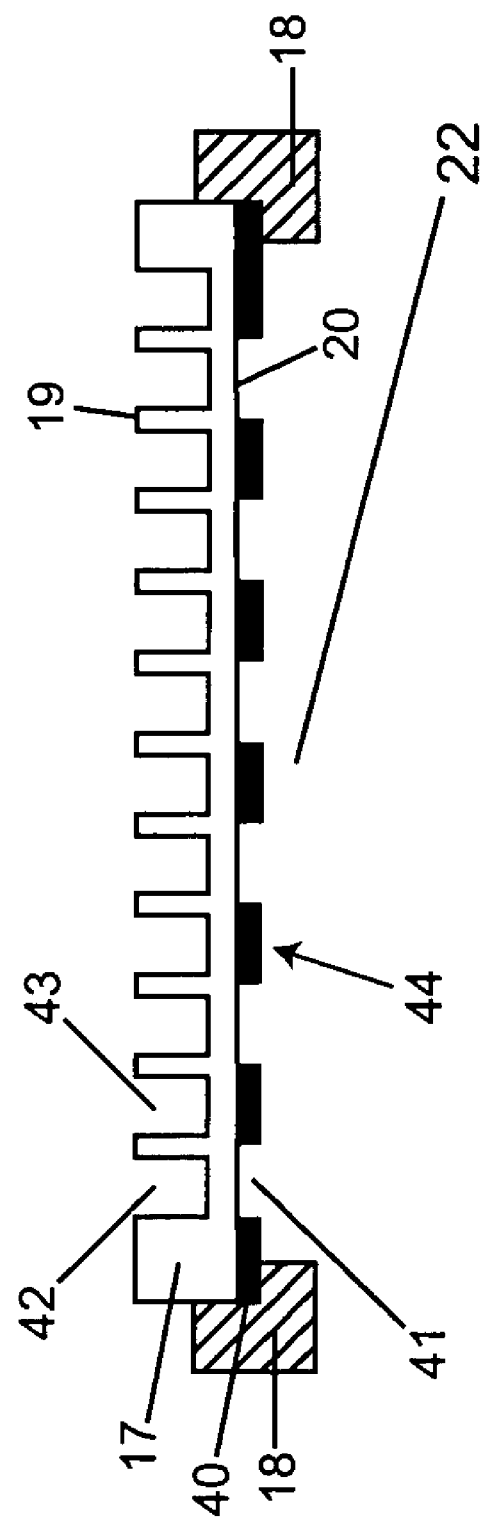

Similarly, in embodiments in which at least one reaction region occupies work area 21, the reaction region optionally comprises a labeled component (which is optionally the same component as the caged component, e.g., kinase sensor 51). The uncaging device can also include a detector that detects a signal from the labeled component. Thus, as illustrated in FIG. 2, apparatus 27 (which has the features of apparatus 1 but also includes additional features) includes optional detector 31 (e.g., a photomultiplier tube, a CCD array, a luminescent or fluorescent plate reader, a cell imager, or the like). In embodiments in which a fluorescent signal is to be detected from the labeled component, the uncaging device can also include an excitation light source that directs excitation light at the reaction region to stimulate the fluorescence. As illustrated, uncaging device 27 also includes data storage system 32, which is coupled to detector 31 and which stores signal intensity measured by detector 31, e.g., signal intensity as a function of location within the work area (e.g., as a function of well location within a multiwell plate) and/or as a function of time after exposure of the work area to uncaging light (i.e., time after uncaging of a caged component). Data storage system 32 can, e.g., be a computer, optionally a computer that also controls operation of the uncaging device.

The uncaging devices of the invention optionally also include other features, e.g., features facilitating high throughput screening and sample processing. Thus, for example, uncaging device 27 includes plate handling element 30 that moves multiwell plate 17 at least from the first fixed position in plate holder 18 to a second fixed position (e.g., on a stack of other plates). Example plate handling elements include, but are not limited to, commercially available robotic plate handling systems such as those available from Beckman Coulter (www.beckman.com), CCS Packard, Inc. (www.ccspackard.com), and Tecan (www.tecan.com). The apparatus optionally also includes a barcode reader (e.g., to conveniently identify individual multiwell plates). Uncaging device 27 optionally also includes fluid handling element 33, which is operably connected to wells 42 and 43 of multiwell plate 17 (the example reaction regions occupying work area 21; expanded view in FIG. 3 Panel D). Fluid handling element 33 can, for example, facilitate the addition and/or removal of various reagents, buffers, and the like to the reaction region(s).

The uncaging devices optionally include environmental controls. For example, apparatus 27 includes heating element 34, which is configured to maintain work area 21 at a selected temperature. The temperature can be selected by a user of the device or preset during manufacture of the device. Additional environmental controls can, for example, maintain a desired atmosphere in the work area (e.g., a selected or preset humidity and/or concentration of $CO_2$, oxygen, argon, nitrogen, or the like).

Safety features can be included in the uncaging devices. For example, apparatus 27 includes safety shield 37, which reduces exposure of a user of the apparatus to the uncaging light. For example, safety shield 37 can prevent exposure of the user to more than 1 $mW/cm^2$ of 365 nm uncaging light at a distance of 30 cm from apparatus 27 (e.g., to more than 0.5 $mW/cm^2$ or even 0.1 $mW/cm^2$). The apparatus optionally includes a safety lock, e.g., a lock that prevents the shutter from opening if the safety shield is not positioned to protect the user.

In some embodiments in which at least one reaction region occupies the work area, the uncaging device comprises a translator that translates the reaction region relative to the uncaging light source and/or a translator that translates the uncaging light source relative to the reaction region. For example, uncaging device 27 includes translator 35 (e.g., an x-y-z translation stage) that translates plate holder 18 and thus multiwell plate 17. Such translators can, for example, be used during reading of signals emanating from the reaction region(s) by a detector, for sequential illumination of reaction regions (e.g., a beam of uncaging light that does not illuminate the entire top or bottom surface of a multiwell plate can be used to scan the plate, by translating either the plate or the light source), or for rotation of the reaction region(s) to ensure even illumination of the reaction region(s).

Masked Multiwell Plates

Another aspect of the invention provides masked multiwell plates, e.g., for use in uncaging of caged components. FIG. 3 schematically illustrates an example masked multiwell plate. Masked multiwell plate 44 includes multiwell plate 17 and mask 40. Mask 40 alters optical power density of uncaging light impinging on at least a first portion (wells 43) of multiwell plate 17. Mask 40 prevents the uncaging light from impinging on the first portion (wells 43) of multiwell plate 17, when the plate is illuminated from below such that the uncaging light impinges on bottom surface 20 of the plate. Apertures 41 in mask 40 permit the uncaging light to impinge on second portion (wells 42) of multiwell plate 17 (e.g., to uncage a caged component in wells 42 but leave the component caged in control wells 43). In other embodiments, the mask can decrease the optical power density of the uncaging light impinging on the first portion of the multiwell plate without completely blocking the uncaging light (e.g., to uncage different proportions of a caged component in different wells of the plate, or to provide an optimal optical energy density for uncaging different caged components in different wells of the plate). As illustrated in FIG. 3, mask 40 is disposed on bottom surface 20 of multiwell plate 17. Alternatively, in embodiments in which the multiwell plate is to be illuminated from above by the uncaging light, the mask can be disposed on top surface 19 of multiwell plate 17. The first portion of the multiwell plate covered by the mask can comprise a portion of at least one well of the multiwell plate, or it can comprise one or more entire wells of the multiwell plate (as in the example illustrated in FIG. 3D, where the first portion of multiwell plate 17 comprises the entirety of each well 42).

Multiwell plate 17 optionally comprises a photoactivatable (e.g., a photolabile) caged component (e.g., one or more photoactivatable components). Exposure to the uncaging light results in uncaging of the caged component (e.g., caged kinase sensor 51 in FIG. 4). As noted for the embodiments described above, the photoactivatable caged component can be a component of essentially any reaction, assay, sample, or the like. The photoactivatable caged component is optionally located inside a cell. The caged component can be essentially any caged compound, molecule, ion, complex, or the like. Caged components include, but are not limited to, caged polypeptides, caged nucleic acids, caged lipids, caged carbohydrates, caged small molecules, and caged metal ions; for example, a caged sensor (e.g., an enzyme or binding sensor), a caged nucleic acid probe, a caged modulator, a caged interfering RNA, a caged RNAi-based sensor, a caged antisense nucleic acid, a caged ribozyme, a caged biomolecular analog, a caged transcription factor, a caged molecular decoy, a caged antibody, a caged aptamer, a caged nucleotide (e.g., a caged nucleoside triphosphate or caged cAMP), a caged chelating agent, a caged fluorescent dye, a caged second messenger, or a caged neurotransmitter.

Uncaging Methods

Another aspect of the invention provides methods, e.g., methods of using the uncaging devices described herein or in which the devices can be used. Thus, one general class of embodiments provides methods of initiating an assay within a reaction area. In the methods, at least one photoactivatable caged component of the assay is introduced into the reaction area (as are any other components necessary for the assay). The reaction area is then exposed to uncaging light, which results in uncaging of the caged component. The optical power density of the uncaging light is substantially uniform over the entire reaction area, which has an area of at least about 50 mm$^2$.

The reaction area can be the work area of an uncaging device of the invention. Similarly, the reaction area can comprise one or more wells of a multiwell plate, sample tubes, channels of a microfluidic chip, capillaries, spots on a two-dimensional array, spots on a three-dimensional array, slides, flow regions of a flow cytometer, or the like. As noted, the reaction area has an area of at least about 50 mm$^2$ (e.g., the area of the reaction area can be greater than 75 mm$^2$, greater than 100 mm$^2$, greater than 10 cm$^2$, greater than 100 cm$^2$, greater than 500 cm$^2$, or even greater than 1000 cm$^2$).

As noted, the optical power density of the uncaging light is substantially uniform over the entire reaction area. Thus, the optical power density of the uncaging light can have a uniformity less than about ±15%, less than about ±10%, less than about ±5%, less than about ±3%, less than about ±1.5%, or less than about ±1% over the entire reaction area.

Using the uncaging devices of the invention, for example, a caged component can be exposed to a precise, predetermined, and reproducible dose of uncaging light to uncage the caged component. Thus, in one class of embodiments, the reaction area is exposed to a desired optical energy density of the uncaging light. Preferably, an actual optical energy density to which the reaction area is exposed is substantially equal to the desired optical energy density. For example, the actual optical energy density preferably varies from the desired optical energy density by less than 10%, less than 5%, or less than 3%.

Exposure to the uncaging light can result in uncaging of substantially all of the caged component present in the reaction area. Alternatively, exposure to the uncaging light can result in uncaging of only a first portion of the caged component present reaction area. If desired, the assay can be repeated without addition of fresh reagents by reexposing the reaction area to the uncaging light and uncaging a second portion of the caged component. The first (and/or second) portion is optionally a defined amount.

The uncaging light can be collimated or not collimated. The optical power density of the uncaging light can be essentially any value useful for uncaging the caged component. Typically, the optical power density of the uncaging light is greater than about 1 mW/cm$^2$ (e.g., greater than about 5 mW/cm$^2$, 10 mW/cm$^2$, 15 mW/cm$^2$, 20 mW/cm$^2$, 30 mW/cm$^2$, or more) and less than about 50,000 mW/cm$^2$ (e.g., less than about 20,000 mW/cm$^2$, 10,000 mW/cm$^2$, 5,000 mW/cm$^2$, or less).

As is known in art, different photoactivatable caging groups have different optimal wavelengths of uncaging light. Thus, the uncaging light can have essentially any wavelength (e.g., the uncaging light can have a wavelength between about 10 nm and about 1000 nm, e.g., between about 60 and about 1000 nm, e.g., between about 300 and about 700 nm). For example, a large number of caging groups are removable by UV light. Thus, in one class of embodiments, the uncaging light has a wavelength in the UV range (e.g., a wavelength between about 10 nm and about 400 nm, e.g., between about 300 nm and about 400 nm). In one class of example embodiments, the uncaging light has a wavelength distribution centered at 365 nm.

In one class of embodiments, the photoactivatable caged component is a photolabile caged component. As noted for the embodiments described above, the photoactivatable caged component can be a component of essentially any reaction, assay, sample, or the like. The photoactivatable caged component is optionally located inside a cell. The caged component can be essentially any caged compound, molecule, ion, complex, or the like. Caged components include, but are not limited to, caged polypeptides, caged nucleic acids, caged lipids, caged carbohydrates, caged small molecules, and caged metal ions; for example, a caged sensor (e.g., an enzyme or binding sensor), a caged nucleic acid probe, a caged modulator, a caged interfering RNA, a caged RNAi-based sensor, a caged antisense nucleic acid, a caged ribozyme, a caged biomolecular analog, a caged transcription factor, a caged molecular decoy, a caged antibody, a caged aptamer, a caged nucleotide (e.g., a caged nucleoside triphosphate or caged cAMP), a caged chelating agent, a caged fluorescent dye, a caged second messenger, or a caged neurotransmitter.

In some embodiments, the reaction area comprises a labeled component (which is optionally the same component as the caged component, e.g., kinase sensor 51), and the methods also include detecting a signal from the labeled component (e.g., a luminescent, fluorescent, or other signal).

EXAMPLES

It is understood that the examples and embodiments described herein are for illustrative purposes only and that various modifications or changes in light thereof will be suggested to persons skilled in the art and are to be included within the spirit and purview of this application and scope of the appended claims. Accordingly, the following examples are offered to illustrate, but not to limit, the claimed invention.

Evaluation of Optical Power Density Uniformity

To determine whether commercially available UV exposure systems can be adapted for use as portions of example uncaging devices (e.g., devices producing uncaging light in the UV wavelength range), uniformity of the light produced by five such commercial devices was evaluated. UV exposure systems tested were Model 66-5 from AB Manufacturing Inc. (ABM, www.abmfg.com), Model LS30/7 from Optical Associates Inc. (OAI, www.oainet.com), Model 82530-1000 from Spectra-Physics' Oriel Division (www.oriel.com), Model PRX500-9 from Taramack Scientific Inc. (www.tamsci.com), and a model from Quintel Corp. (www.quintelcorp.com).

Figure 5A:
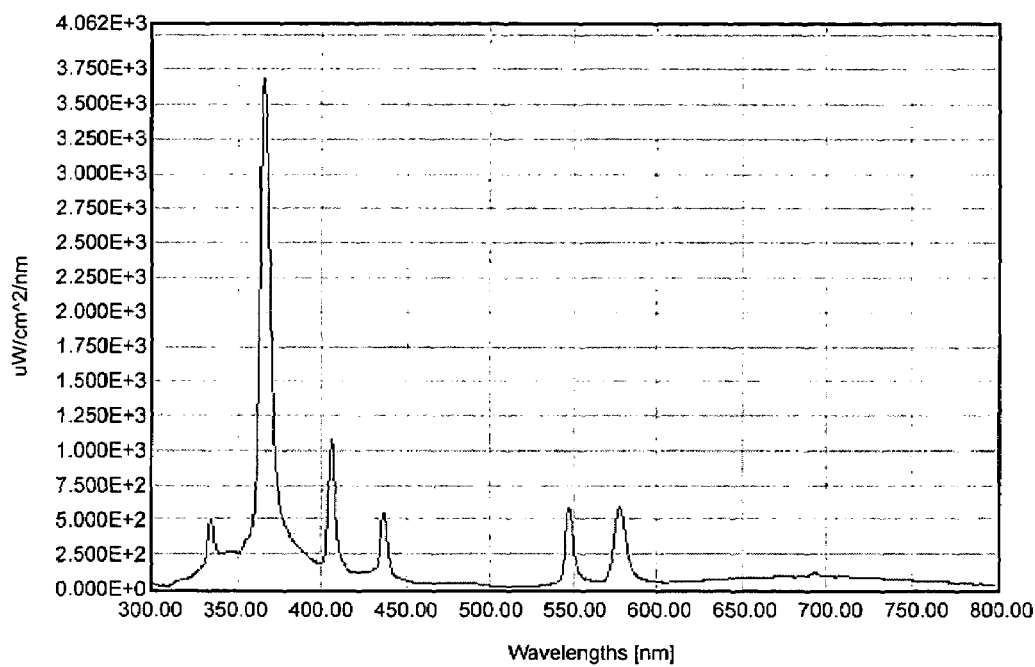
FIG. 5 presents an optical spectrum of output light from the ABM UV exposure system without a 365 nm filter (Panel A) and with a 365 nm filter (Panel B).
Figure 5B:
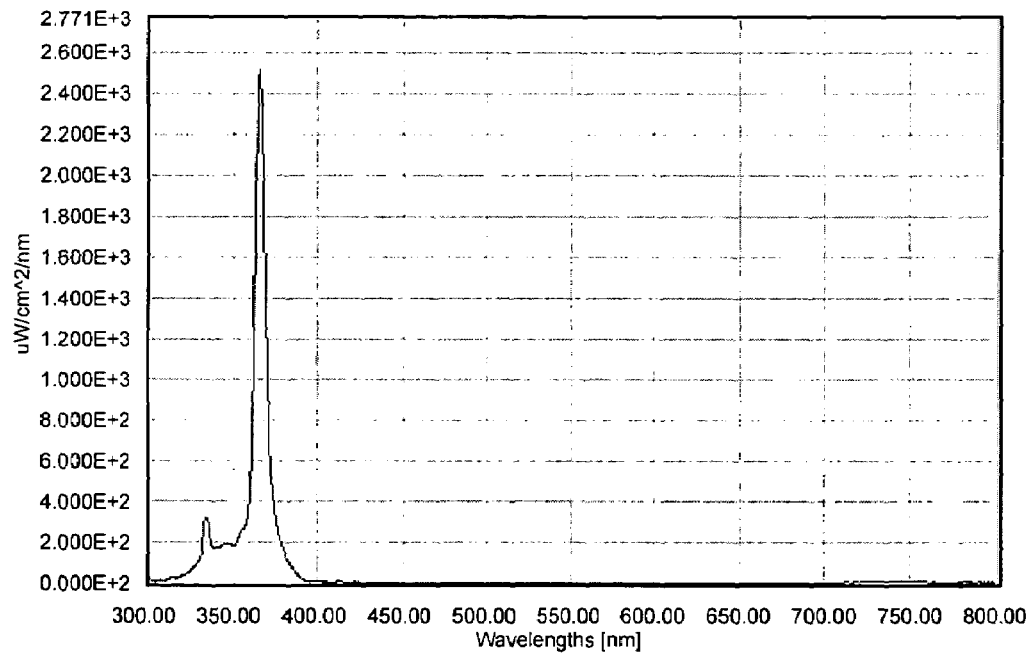

The systems were operated in constant intensity mode with a 365 nm filter in place (constant power mode was also tested). FIG. 5 Panel A presents an optical spectrum of output light from the ABM system without a 365 nm filter, while Panel B presents an optical spectrum of output light from the same system with the 365 nm filter. With the filter, the output light has a wavelength distribution that is centered at 365 nm. Optical power density of the output light (with a 365 nm filter) ranged from 7.3 mW/cm$^2$ to 39 mW/cm$^2$ for the five systems tested.

Figure 6:
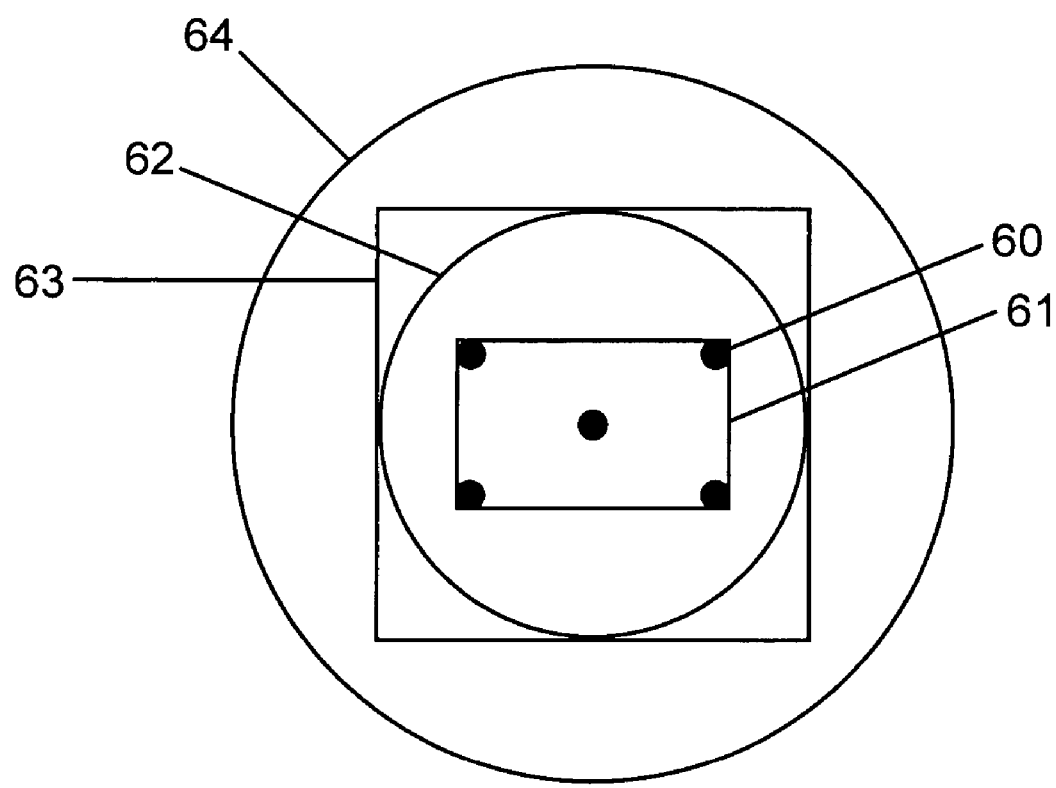
FIG. 6 schematically depicts optical power density meter probe positions within a typical multiwell plate footprint. Exposure areas of three UV exposure systems are also indicated.

Uniformity of the optical power density of the output light at 365 nm was measured using a "five point" method. As illustrated in FIG. 6, the optical power densities at 365 nm were measured at the center and each corner of a typical multiwell plate footprint. Optical power density meter probe positions are indicated by filled circles 60 at five points within typical multiwell plate footprint 61 (which has dimensions of about 4.3 by 3 inches). The exposure areas of the OAI system (62, about 6 inches in diameter), the ABM system (63, about 6 by 6 inches), and the Oriel system (64, about 10 inches in diameter) are indicated for reference. Uniformity is calculated using the formula Uniformity=+/−(max−min)/(max+min), where max is the maximum optical power density and min is the minimum optical power density, and presented as a +/− percentage value. The resulting uniformities for the five systems are listed in Table 1.

TABLE 1

| | Optical power density uniformity | | | | |
|---|---|---|---|---|---|
| system | ABM | OAI | Oriel | Taramack | Quintel |
| uniformity | +/−1.5% | +/−2.5% | +/−2.8% | +/−4.2% | +/−5.0% |

Uniformity of the optical power density of the output light was also measured by a scanning method. A linear stage was set up to scan a 6 by 6 inch test area in 9 mm steps. Measured uniformities were very similar to those measured by the five point method.

Device for Photoactivation and Detection of Biochemical and Cell-Based Assays

Caged molecules have been used in microscopy studies of cells. There are commercial devices for uncaging samples on microscope slides. For example, Photonics Micropoint System and Prairie Technology fluorescent microscope adaptors have been used to activate caged calcium ions or EDTA for studying ion channels and voltage clamps in a single cell. However, there is currently no commercially available system for uncaging samples in test tube, microtiter plate, or other formats. Researchers resort to homemade xenon or mercury flash or UV lamps, which are highly non-uniform, irreproducible from run-to-run, not user friendly and unsafe to use. They are not integrated with a reader and are not made for high throughput applications.

This invention describes an uncaging device that can trigger photoactivatable biochemical and cell-based assays and that optionally also detects signals from the assays. Photoactivatable assays contain caged molecules whose activities are muted by the attachment of photoactivatable (e.g., photolabile) chemical groups. When exposed to uncaging light, the photolabile groups fall off and the uncaged molecule becomes functionally active, setting off the reaction and generating signals.

Preferably, the uncaging device produces light of specific wavelength and intensity aiming at specific locations. For example, the device can initiate a photoactivatable reaction over an area ranging from about a nanometer to about a meter in size. It can trigger a single reaction or many reactions, with a spatial resolution of, e.g., 1 millimeter, 500 microns, 100 microns, 50 microns, 20 microns, 10 microns, or less. It can trigger photoactivatable reactions at high speed, preferably within 100 milliseconds, 10 milliseconds, 1 millisecond, 100 microseconds, 10 microseconds, 1 microsecond, 100 nanoseconds, 10 nanoseconds, or 1 nanosecond or less, for example. The uncaging device also has the capability of detecting the signal from the reaction in synchrony with the triggering event.

In a preferred embodiment, this device is coupled with a robotic liquid handling machine to provide an integrated platform for bioassays, including high throughput screening of compound libraries in drug discovery or clinical diagnosis of patient samples.

Example Instrument Functions and Capabilities

Figure 7:
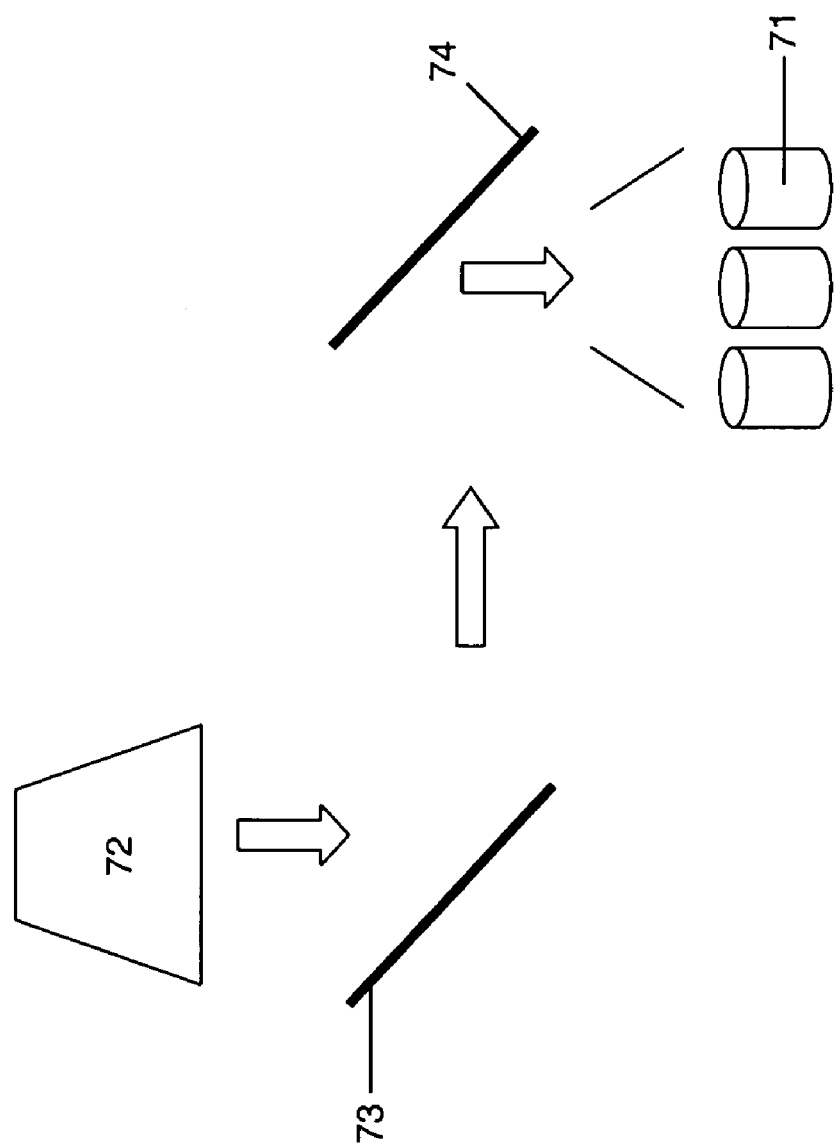
FIG. 7 schematically depicts uncaging using top illumination. In this example, illumination is provided from the top of the wells of a multiwell plate, e.g., for uncaging a sensor in solution to perform a biochemical assay.
Figure 8:
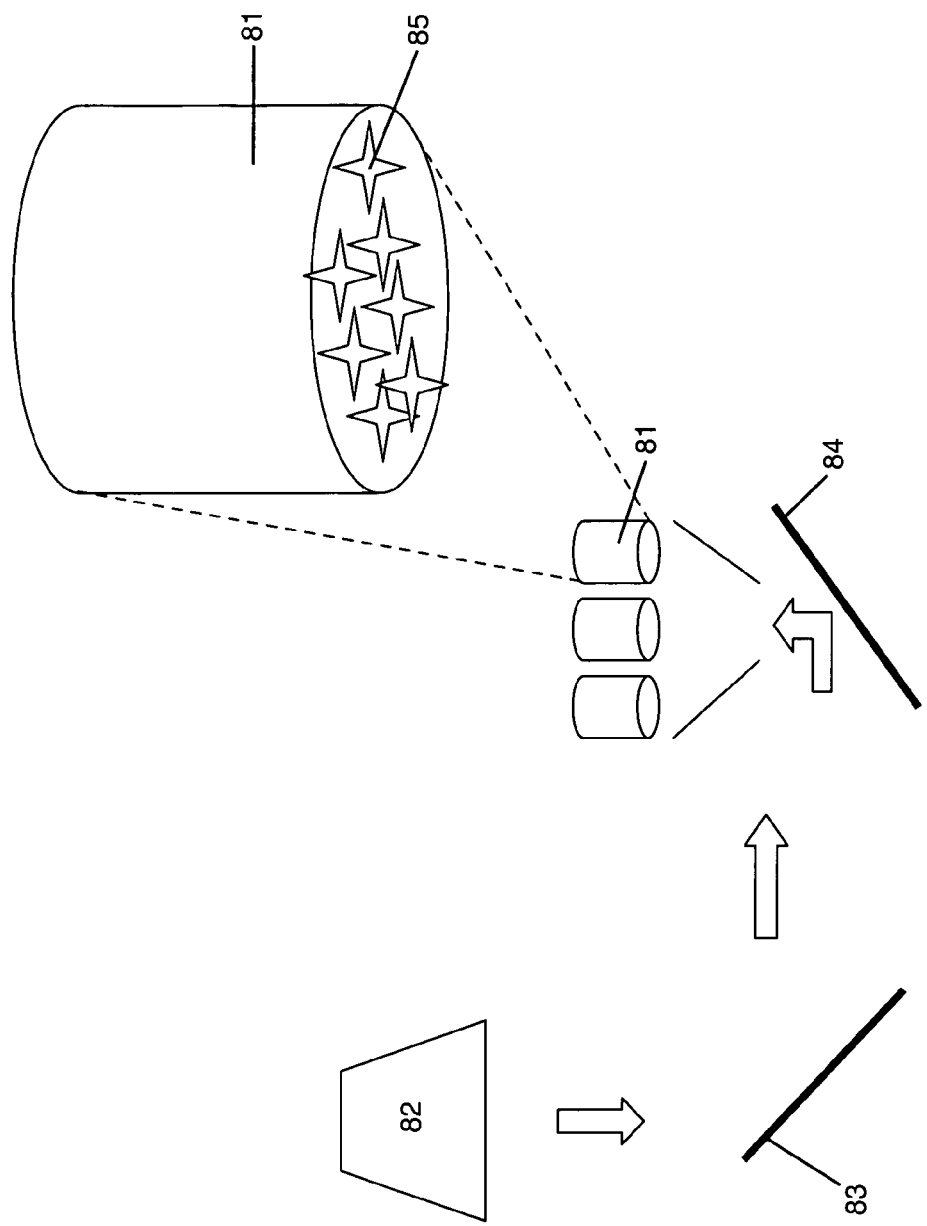
FIG. 8 schematically depicts uncaging using bottom illumination. In this example, illumination is provided from the bottom of the wells of a multiwell plate, e.g., for uncaging a sensor in adherent cells.
Figure 9:
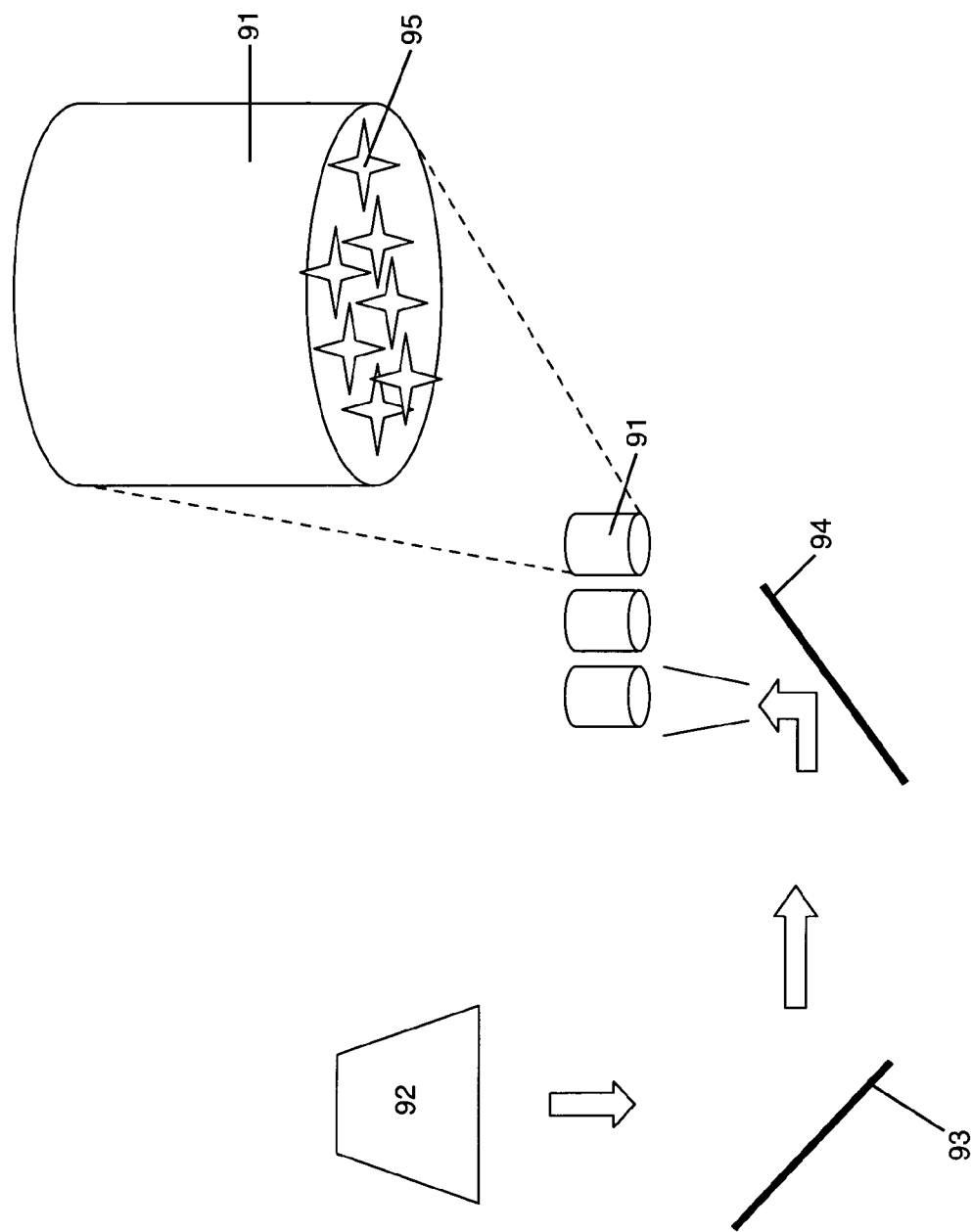
FIG. 9 schematically depicts uncaging using bottom illumination to each well. In this example, illumination is provided to a single well at a time, e.g., from the bottom of the wells, e.g., for uncaging a sensor in adherent cells.
Figure 10:
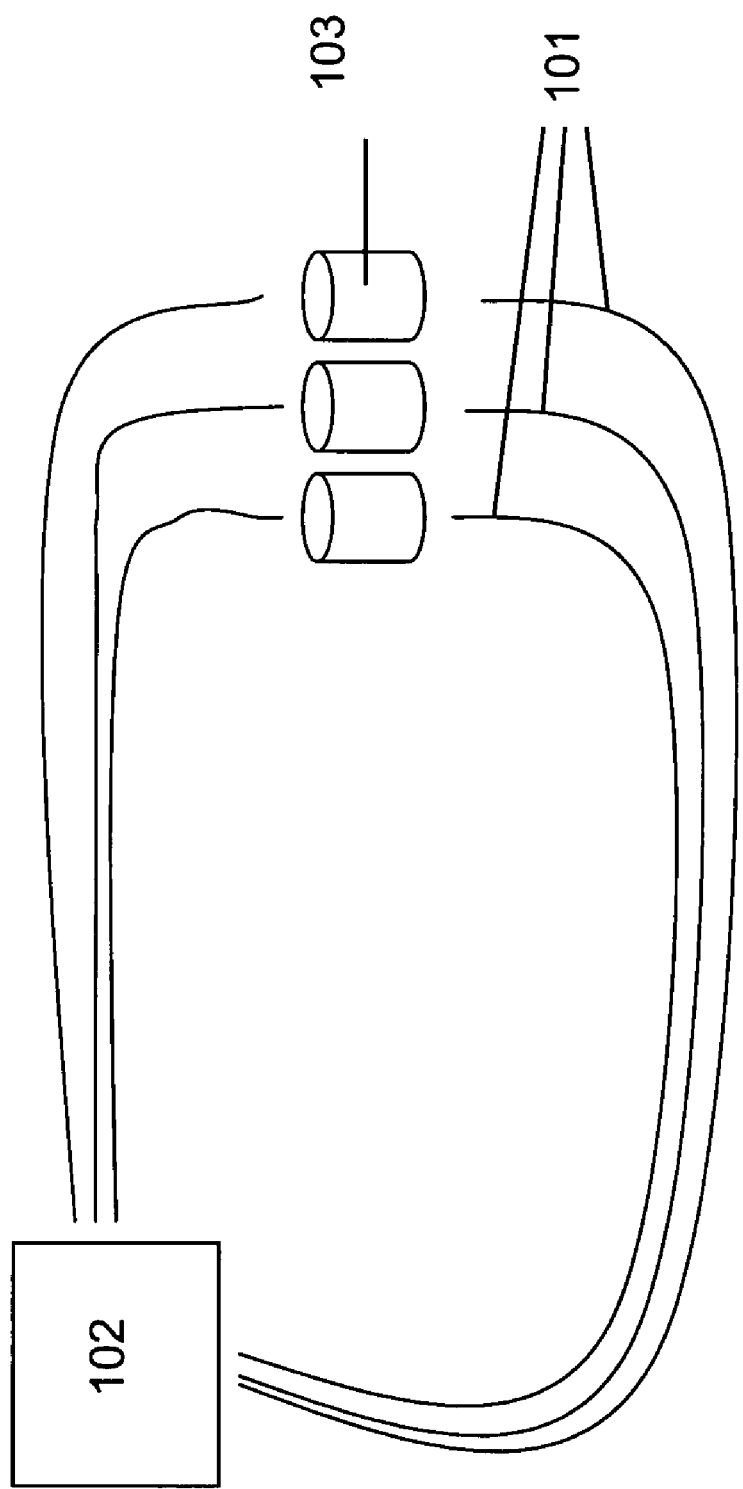
FIG. 10 schematically illustrates fiber optic bundles used to guide uncaging light to the wells of a multiwell plate. As depicted, illumination can be provided to the top and/or bottom of the wells (singly or in any combination).
Figure 11:
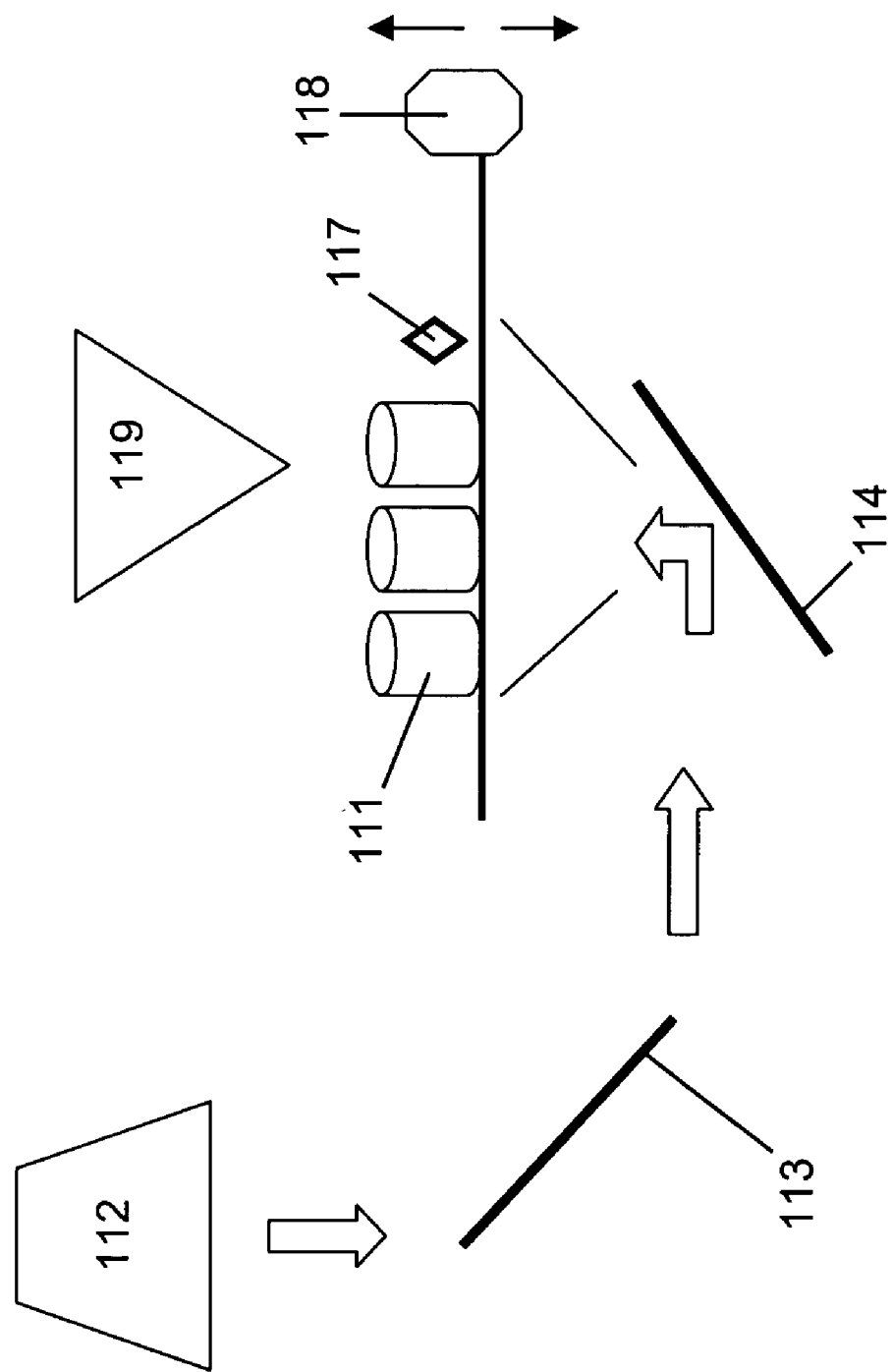
FIG. 11 schematically depicts automatic identification of optimal uncaging distance.
Figure 12A:
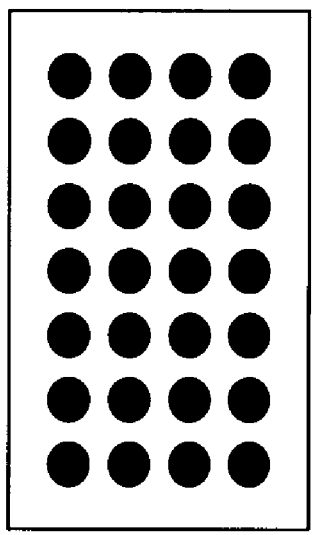
FIG. 12 schematically illustrates example formats suitable for uncaging: multiwell plate (e.g., 96, 384, 1536, or 3456 wells; Panel A), two-dimensional microarray of cells or biochemical assays (Panel B), three-dimensional microarray of cells or biochemical assays (Panel C), and capillary or flow channel (Panel D).
Figure 12B:
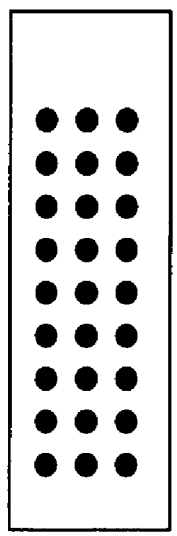
Figure 12C:
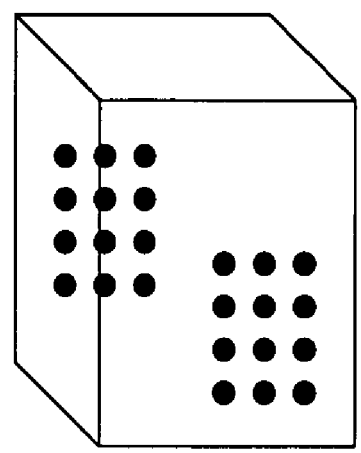
Figure 12D:
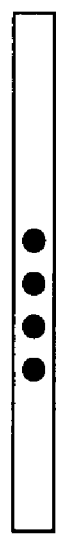

This invention features an uncaging instrument that optionally has a plurality of the following capabilities: (1) Photo-activate biochemical and cell based assays and detect the results of the assays at the same time (FIGS. 7-11). (2) Uncage in standard reaction formats such as multiwell plates (e.g., 96, 384 and 1536 well microtiter plates; FIG. 12 Panel A). (3) Uncage other reaction formats such as two-dimensional microarrays of cells or biochemical assays (FIG. 12 Panel B), three-dimensional microarrays of cells or biochemical assays (FIG. 12 Panel C), assays within micro channels of micro fluidic systems (FIG. 12 Panel D) or flow channels of flow cytometers (FIG. 13), etc. (4) Control energy, wavelength, time, location (x, y, z) and dimension of illumination for uncaging and optionally detection (FIG. 11). (5) Illuminate from different orientations, e.g., top, bottom and side. (FIGS. 7-8). (6) Auto calibrate for reproducible illumination of light within and between experiments (FIG. 11). (7) Adjust the height of sample location (FIG. 11). (8) Rotate samples to ensure even illumination. (9) Energy and wavelength calibration meter. (10) Various detectors for measuring output signal (e.g., photo multiplier tube for detecting fluorescent or chemiluminescent signal). (11) Computer and instrument software. (12) Uniform illumination. (13) Heating and environmental control (e.g., for maintaining or stimulating cell culture). (14) Liquid handling for precision delivery of test compounds.

For example, in one example class of embodiments, an uncaging apparatus includes at least one reaction region that comprises at least one photoactivatable caged component of the assay (e.g., a photolabile caged component), a light source for directing light at the reaction region or a portion thereof, and a detector for detecting at least one signal produced by at least one labeled component of the assay. The light from the light source is capable of uncaging the photoactivatable caged component. The reaction region can comprise, e.g., a well of a multiwell microtiter plate, a sample tube, a channel of a microfluidic chip, a capillary, a spot on a two-dimensional array, or a spot on a three-dimensional array. Preferably, the apparatus also includes a fluid-handling element.

Example Instrument Description

The instrument typically has illumination sources for uncaging, stimulation and/or detection, a mechanism to control the illumination power and/or energy density, and an optical set-up to guide the light from illumination source to sample. A calibration light meter can be used to ensure reproducible exposure and automated power and location adjustments. Mechanical design can be used to manipulate samples and/or optics in an x, y or z direction depending on specific application and assay format. A liquid handling mechanism is preferably integrated into the reaction holder.

Figure 14:
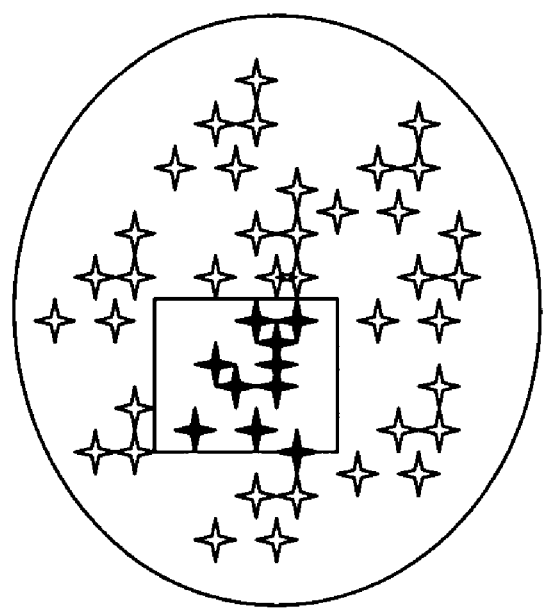
FIG. 14 schematically depicts uncaging a smaller region within a well of a microtiter plate. Panel A depicts cells (white stars) grown on the bottom of the well. Panel B depicts light exposure of a portion of the well (boxed area), which uncages a caged molecule inside the cells. At the same time, detection of a signal from the same portion of the well (from the cells containing the uncaged molecule, represented by black stars) is performed.
Figure 14:
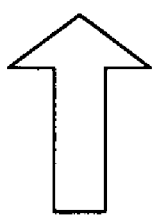
Figure 14:
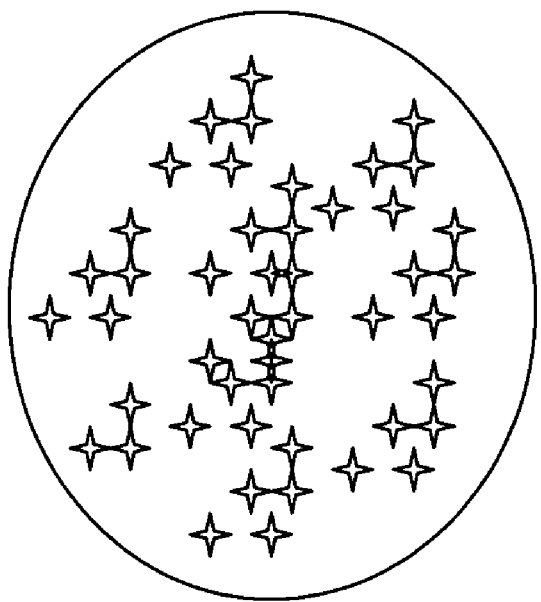
Figure 15B:
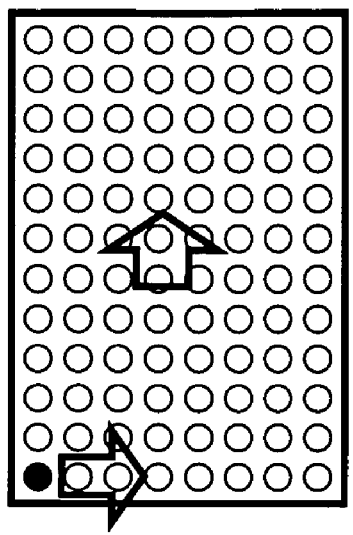
FIG. 15 Panel A schematically depicts an uncaging device. Panels B-D schematically depict different example fiber optic setups and scanning modes.
Figure 15C:
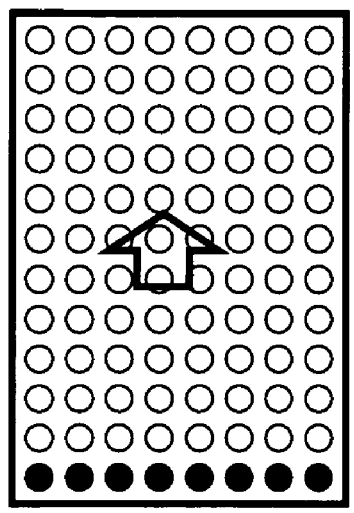
Figure 15D:
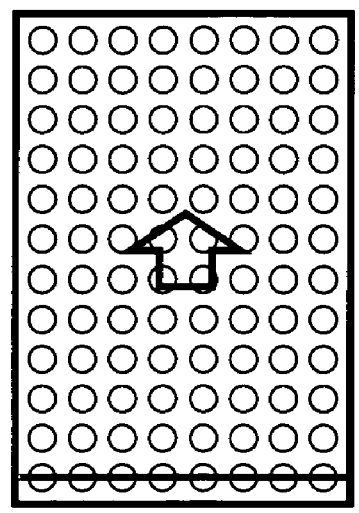
Figure 15A:
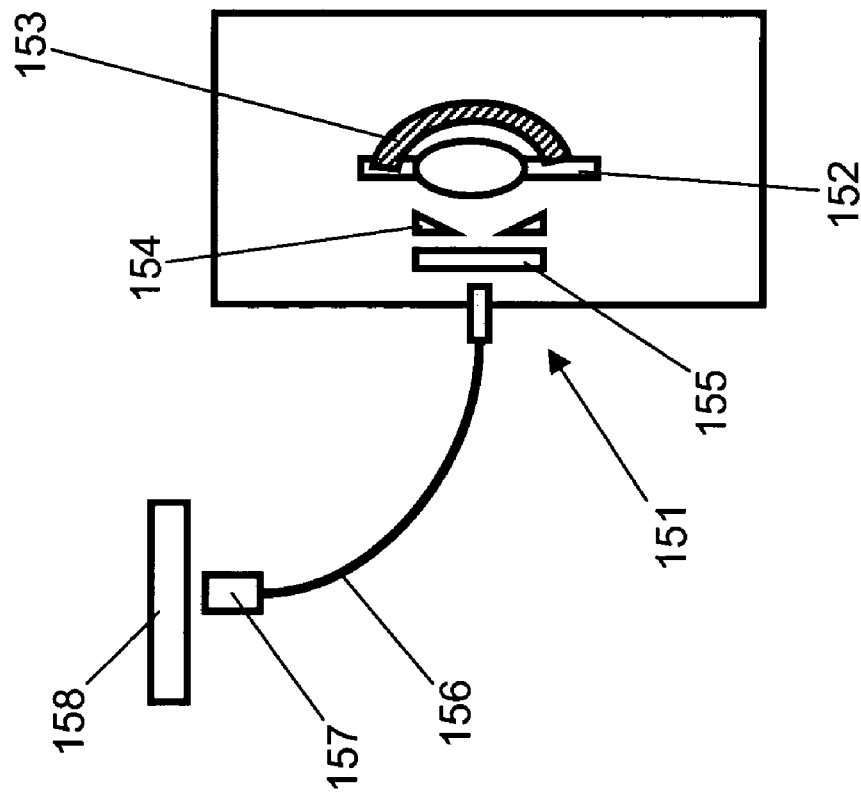

The illumination source(s) can be, e.g., continuous or pulse lasers, flash lamps (e.g., Xenon or Mercury), continuous lamps and others. The light can be guided to the sample with one or more optical mirror, lens, fiber optic bundle, or the like. Illumination dimension (focus or broad beam) can be controlled using lenses or mirrors, for example. Uniform illumination can be achieved, e.g., by using a collimated lens. For a non-uniform light source, samples or the light source can be rotated to ensure even exposure of all samples. A diffuser can also be used to ensure even illumination. As an alternative example, fiber optic guided light can be directed to each well of a multiwell plate to uncage the entire well or only part of a well. FIG. 10 schematically illustrates fiber optic bundles 101 used to guide uncaging light from light source 102 to wells 103 of a multiwell plate. As depicted, illumination can be provided to the top and/or bottom of the wells (singly or in any combination). A light source with less energy can be used for uncaging a small part of a well in microtiter plate. The detection is then focused on the uncaged region of the well. Hence, uncaging a smaller part of a well can permit the use of a lower energy light source. FIG. 14 schematically depicts uncaging a smaller region within a well of a microtiter plate. Panel A depicts cells (white stars) grown on the bottom of the well. Panel B depicts light exposure of a portion of the well (boxed area), which uncages a caged molecule inside the cells. At the same time, detection of a signal from the same portion of the well (from the cells containing the uncaged molecule, represented by black stars) is performed.

After the samples (biochemical reactions or adherent or non-adherent cells) are photoactivated, the samples can be read on various detectors such as a microtiter plate reader (commercially available from many vendors), a flow cytometer (commercially available from, e.g., Beckman Coulter or BD Biosciences), a laser scanning cytometer (commercially available from, e.g., Acumen, Cellomics or Amersham), a fluorescent microscope (commercially available from, e.g., Nikon, Zeiss, Olympus and others), a confocal fluorescent microscope (commercially available from, e.g., Bio-Rad, Zeiss and others) or microfluidic chip systems (commercially available from, e.g., Caliper and others).

Figure 13:
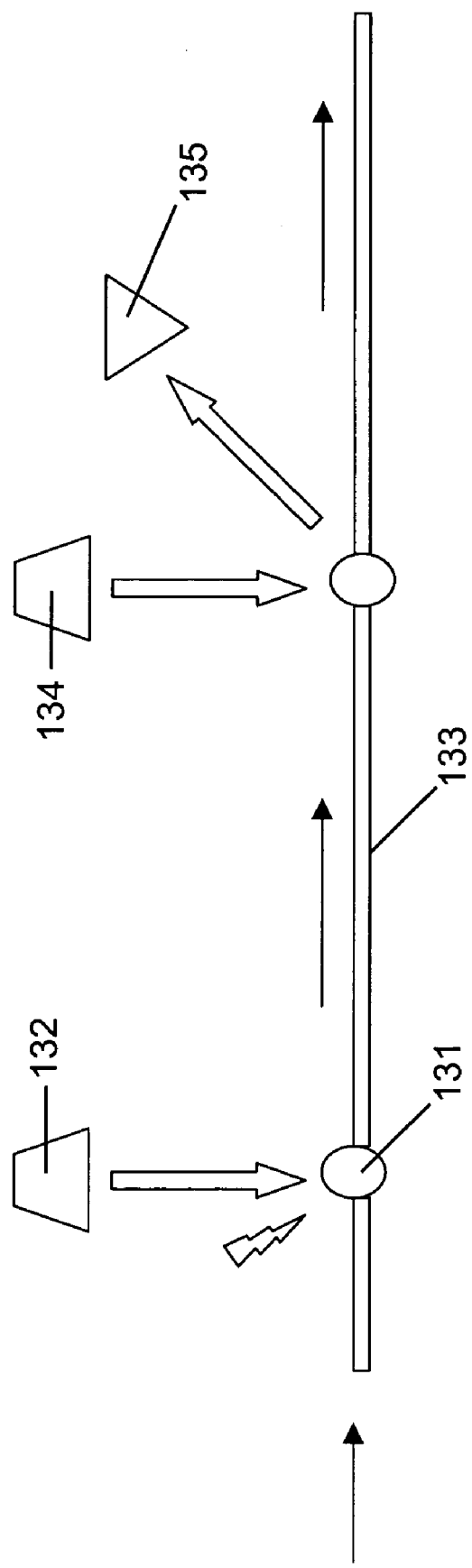
FIG. 13 schematically depicts uncaging in a flow cytometer.

An uncaging illumination source can be incorporated into any of the instruments listed above. For example, an uncaging illumination source can be incorporated into a microtiter plate reader so that photoactivation of samples can be immediately followed by detection—permitting precise control of kinetic reading. For a flow cytometer, samples can be photoactivated by flowing the samples past an uncaging light source before they reach the detector location. For example, activation of non-adherent cells can be performed in high throughput mode using photoactivation flow cytometer devices. As the cells flow pass the light source, they are activated one at a time before going to the detector. FIG. 13 schematically depicts uncaging in a flow cytometer. Cell 131 comprising a caged component and flowing in channel 133 in the direction of the solid arrows is exposed to uncaging light from uncaging light source 132. Cell 131, now comprising the uncaged, active component, is exposed to excitation light from excitation light source 134, and a fluorescent signal emitted from the component is detected by detector 135.

Non-fluorescent probes can also be employed with a photoactivation device. For example, a chemiluminescent reaction can be triggered using a light activated sensor/regulator.

Illumination from the top of the wells is preferred for many applications, such as some biochemical assays or uncaging in cells in suspension (illumination from the bottom or side of the wells may be preferred for many other applications, such as uncaging in adherent cells). Small assay volumes and areas are typically preferred in photoactivatable assays since less energy per area is required. For example, a 1536 well assay format is more ideal than 96 and 384 well assay formats. In addition, a shallow assay reaction is preferred since light transmission through the assay buffer can be poor, especially for shorter wavelength light. FIG. 7 schematically depicts uncaging using illumination from the top of sample wells 71 of a multiwell plate. Uncaging light provided by light source 72 is reflected by mirrors 73 and 74 as indicated by the open arrows. FIG. 8 schematically depicts uncaging using illumination from the bottom of wells 81 of a multiwell plate. Uncaging light provided by light source 82 is reflected by mirrors 83 and 84 as indicated by the open arrows. The uncaging light impinges on the bottom of wells 81, e.g., for uncaging a sensor in adherent cells 85 comprising the sensor. FIG. 9 schematically depicts uncaging using illumination from the bottom of wells 91, where illumination is provided to a single well at a time. Uncaging light provided by light source 92 is reflected by mirrors 93 and 94 as indicated by the open arrows. The uncaging light impinges on the bottom of well 91, e.g., for uncaging a sensor in adherent cells 95 comprising the sensor. FIG. 11 schematically depicts automatic identification of optimal distance from the light source for uncaging in sample wells. Uncaging light provided by light source 112 is reflected by mirrors 113 and 114 as indicated by the open arrows. The uncaging light impinges on the bottom of wells 111. Light meter 117, which is located in the same plane as sample wells 111, monitors the uncaging light. Motor 118 adjusts the position (e.g., the vertical and/or horizontal position) of sample wells 111 and meter 117 with respect to the beam of uncaging light, e.g., to position the wells in the most intense part of the beam. Optional detector 119 detects a signal emitted from sample wells 111 (e.g., from a sensor in the wells).

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

What is claimed is:

1. An apparatus, comprising:
a work area;
an uncaging light source that directs uncaging light at the work area or a selected portion thereof, wherein the uncaging light has an optical power density greater than 100 $\mu W/cm^2$ at one or more wavelengths between about 100 nm and about 400 nm;
a multiwell plate; and,
a plate holder configured to accept the multiwell plate in a first fixed position, wherein the multiwell plate in the first fixed position occupies the work area, wherein the multiwell plate comprises a photoactivatable caged component, and wherein exposure to the uncaging light results in uncaging of the caged component.

2. The apparatus of claim 1, wherein the photoactivatable caged component is a photolabile caged component.

3. The apparatus of claim 1, wherein optical power density of the uncaging light is substantially uniform over the entire work area.

4. The apparatus of claim 3, wherein optical power density of the uncaging light has a uniformity less than about ±15%, less than about ±10%, less than about ±5%, less than about ±3%, or less than about ±1.5% over the entire work area.

5. The apparatus of claim 1, wherein the optical power density of the uncaging light is greater than about 300 $\mu W/cm^2$ at one or more wavelengths between about 100 nm and about 400 nm.

6. The apparatus of claim 1, wherein optical power density of the uncaging light is greater than about 1 $mW/cm^2$ and less than about 50,000 $mW/cm^2$.

7. The apparatus of claim 1, wherein the uncaging light has a wavelength between about 300 nm and about 400 nm.

8. The apparatus of claim 1, wherein the uncaging light has a wavelength selected by a user of the apparatus.

9. The apparatus of claim 1, wherein the uncaging light is collimated.

10. The apparatus of claim 1, wherein the uncaging light is not collimated.

11. The apparatus of claim 1, further comprising an optical meter that monitors the uncaging light.

12. The apparatus of claim 11, wherein the optical meter comprises an optical power density meter, an optical power meter, an optical energy density meter, or an optical energy meter.

13. The apparatus of claim 1, wherein the area of the work area or the selected portion thereof is greater than 25 $\mu m^2$.

14. The apparatus of claim 1, wherein the area of the work area or the selected portion thereof is less than 3 $cm^2$.

15. The apparatus of claim 1, wherein the uncaging light impinges on a bottom surface of the multiwell plate.

16. The apparatus of claim 1, wherein the uncaging light impinges on a top surface of the multiwell plate.

17. The apparatus of claim 1, further comprising a plate handling element that moves the multiwell plate at least from the first fixed position to a second fixed position.

18. The apparatus of claim 1, wherein the plate holder is configured to accept a mask, the mask altering optical power density of the uncaging light impinging on at least a first portion of the multiwell plate.

19. The apparatus of claim 18, wherein the mask prevents the uncaging light from impinging on at least the first portion of the multiwell plate and permits the uncaging light to impinge on at least a second portion of the multiwell plate.

20. The apparatus of claim 1, wherein the apparatus further comprises an exposure controller that controls optical energy density of the uncaging light to which the work area or the selected portion thereof is exposed.

21. The apparatus of claim 20, wherein the exposure controller controls the optical energy density of the uncaging light by controlling optical power density of the uncaging light and/or an exposure time, which exposure time is an amount of time to which the work area or the selected portion thereof is exposed to the uncaging light.

22. The apparatus of claim 21, wherein the exposure controller accepts an input from a user of the apparatus, which input indicates a desired exposure time.

23. The apparatus of claim 21, wherein the exposure controller accepts an input from a user of the apparatus, which input indicates a desired optical energy density.

24. The apparatus of claim 23, further comprising an optical meter, wherein the exposure controller accepts a signal from the optical meter.

25. The apparatus of claim 24, wherein the exposure controller uses the signal from the optical meter to adjust the exposure time to achieve the desired optical energy density.

26. The apparatus of claim 23, wherein an actual optical energy density to which the work area or the selected portion thereof is exposed is substantially equal to the desired optical energy density.

27. The apparatus of claim 26, wherein the actual optical energy density varies from the desired optical energy density by less than 10%.

28. The apparatus of claim 26, wherein the actual optical energy density varies from the desired optical energy density by less than 5%.

29. The apparatus of claim 1, wherein the apparatus further comprises a safety shield, which safety shield reduces exposure of a user of the apparatus to the uncaging light.

30. The apparatus of claim 1, wherein the multiwell plate comprises a labeled component, further comprising a detector that detects a signal from the labeled component.

31. The apparatus of claim 30, further comprising a data storage system that stores signal intensity measured by the detector, the data storage system being coupled to the detector.

32. The apparatus of claim 30, further comprising a computer that controls operation of the apparatus and records signal intensity measured by the detector.

33. The apparatus of claim 1, further comprising a heating element configured to maintain the work area at a selected temperature.

34. The apparatus of claim 1, further comprising a fluid-handling element operably connected to the multiwell plate.

35. The apparatus of claim 1, further comprising a translator that translates the multiwell plate relative to the uncaging light source and/or a translator that translates the uncaging light source relative to the multiwell plate.

36. A method of initiating an assay within a reaction area, the method comprising:
    introducing at least one photoactivatable caged component of the assay into the reaction area, wherein the reaction area has an area of at least about 50 mm$^2$; and,
    exposing the reaction area to uncaging light, the optical power density of the uncaging light being substantially uniform over the entire reaction area, whereby exposure to the uncaging light results in uncaging of the caged component.

37. The method of claim 36, wherein the optical power density of the uncaging light has a uniformity less than about ±15%, less than about ±10%, less than about ±5% less than about ±3%, or less than about ±1.5% over the entire reaction area.

38. The method of claim 36, wherein exposing the reaction area to uncaging light comprises exposing the reaction area to a desired optical energy density of the uncaging light.

39. The method of claim 38, wherein an actual optical energy density to which the reaction area is exposed is substantially equal to the desired optical energy density.

40. The method of claim 39, wherein the actual optical energy density varies from the desired optical energy density by less than 10%, less than 5%, or less than 3%.

41. The method of claim 36, wherein the uncaging light is collimated.

42. The method of claim 36, wherein the uncaging light is not collimated.

43. The method of claim 36, wherein the optical power density of the uncaging light is greater than about 1 mW/cm$^2$ and less than about 50,000 mW/cm$^2$.

44. The method of claim 36, wherein the uncaging light has a wavelength between about 300 nm and about 700 nm.

45. The method of claim 36, wherein the reaction area comprises one or more wells of a multiwell plate, sample tubes, channels of a microfluidic chip, capillaries, spots on a two-dimensional array, or spots on a three-dimensional array.

46. The method of claim 36, wherein the area of the reaction area is greater than 75 mm$^2$.

47. The method of claim 36, wherein the photoactivatable caged component is a photolabile caged component.

48. The method of claim 36, wherein the caged component comprises one or more of: a caged polypeptide, a caged nucleic acid, a caged small molecule, a caged nucleoside triphosphate, a caged chelating agent, or a caged metal ion.

49. The method of claim 36, wherein the caged component comprises a caged sensor, a caged nucleic acid probe, a caged modulator, a caged interfering RNA, a caged antisense nucleic acid, a caged ribozyme, a caged biomolecular analog, a caged transcription factor, a caged molecular decoy, a caged antibody, or a caged aptamer.

50. The method of claim 36, wherein the reaction area comprises a labeled component, further comprising detecting a signal from the labeled component.

51. The apparatus of claim 1, wherein the optical power density$_2$ of the uncaging light is greater than about 500 μW/cm$^2$ at one or more wavelengths between about 100 nm and about 400 nm.

52. The apparatus of claim 1, wherein the optical power density$_2$ of the uncaging light is greater than about 700 μW/cm$^2$ at one or more wavelengths between about 100 nm and about 400 nm.

53. The apparatus of claim 1, wherein the optical power density$_2$ of the uncaging light is greater than about 900 μW/cm$^2$ at one or more wavelengths between about 100 nm and about 400 nm.

54. The apparatus of claim 1, wherein the area of the work area or the selected portion thereof is greater than 0.01 mm$^2$.

55. The apparatus of claim 1, wherein the area of the work area or the selected portion thereof is greater than 1 mm$^2$.

56. The apparatus of claim 1, wherein the area of the work area or the selected portion thereof is greater than 100 mm$^2$.

57. The apparatus of claim 1, wherein the area of the work area or the selected portion thereof is greater than 10 cm$^2$.

58. The apparatus of claim 1, wherein the area of the work area or the selected portion thereof is greater than 100 cm$^2$.

59. The apparatus of claim 1, wherein the area of the work area or the selected portion thereof is greater than 500 cm$^2$.

60. The apparatus of claim 1, wherein the area of the work area or the selected portion thereof is less than 100 mm$^2$.

61. The apparatus of claim 1, wherein the area of the work area or the selected portion thereof is less than 10 mm$^2$.

62. The apparatus of claim 1, wherein the area of the work area or the selected portion thereof is less than 1.5 mm$^2$.

63. The apparatus of claim 1, wherein the area of the work area or the selected portion thereof is less than 0.1 mm$^2$.

64. The apparatus of claim 1, wherein the area of the work area or the selected portion thereof is less than 0.25 mm$^2$.

65. The apparatus of claim 1, wherein the area of the work area or the selected portion thereof is less than 2500 μm$^2$.

66. The apparatus of claim 1, wherein the area of the work area or the selected portion thereof is less than 50 μm$^2$.

67. The method of claim 36, wherein the uncaging light has a wavelength between about 300 nm and about 400 nm.

68. The method of claim 36, wherein the area of the reaction area is greater than 100 mm$^2$.

69. The method of claim 36, wherein the area of the reaction area is greater than 10 cm$^2$.

70. The method of claim 36, wherein the area of the reaction area is greater than 100 cm$^2$.

71. The method of claim 36, wherein the area of the reaction area is greater than 500 cm$^2$.

* * * * *